(12) United States Patent
Levin et al.

(10) Patent No.: US 8,888,811 B2
(45) Date of Patent: Nov. 18, 2014

(54) DEVICE AND METHOD FOR ATTACHING AN IMPLANT TO BIOLOGICAL TISSUE

(75) Inventors: Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 557 days.

(21) Appl. No.: 12/834,538

(22) Filed: Jul. 12, 2010

(65) Prior Publication Data
US 2010/0318121 A1    Dec. 16, 2010

Related U.S. Application Data

(63) Continuation-in-part of application No. PCT/IL2009/000985, filed on Oct. 20, 2009.

(60) Provisional application No. 61/106,616, filed on Oct. 20, 2008.

(51) Int. Cl.
  *A61B 17/08* (2006.01)
  *A61B 17/00* (2006.01)
  *A61F 2/00* (2006.01)

(52) U.S. Cl.
  CPC ....... *A61B 17/00491* (2013.01); *A61B 17/0057* (2013.01); *A61F 2/0063* (2013.01); *A61B 17/00234* (2013.01); *A61B 2017/00597* (2013.01); *A61B 2017/00623* (2013.01); *A61B 2017/00659* (2013.01); *A61F 2002/0072* (2013.01)
  USPC ............ 606/213; 606/151; 606/214; 606/215

(58) Field of Classification Search
  None
  See application file for complete search history.

(56) References Cited

U.S. PATENT DOCUMENTS

| | | | |
|---|---|---|---|
| 4,347,847 A |   | 9/1982 | Usher |
| 4,359,049 A | * | 11/1982 | Redl et al. .................... 604/82 |
| 4,400,833 A |   | 8/1983 | Kurland |
| 4,452,245 A |   | 6/1984 | Usher |
| 4,485,816 A |   | 12/1984 | Krumme |
| 4,585,458 A |   | 4/1986 | Kurland |
| 4,633,873 A |   | 1/1987 | Dumican et al. |
| 4,838,884 A |   | 6/1989 | Dumican et al. |
| 4,854,316 A |   | 8/1989 | Davis |
| 5,019,096 A |   | 5/1991 | Fox, Jr. et al. |
| 5,116,357 A |   | 5/1992 | Eberbach |
| 5,122,155 A |   | 6/1992 | Eberbach |
| 5,125,553 A |   | 6/1992 | Oddsen et al. |
| 5,141,515 A |   | 8/1992 | Eberbach |
| 5,147,374 A |   | 9/1992 | Fernandez |

(Continued)

FOREIGN PATENT DOCUMENTS

| | | |
|---|---|---|
| CA | 2413904 A1 | 10/2003 |
| EP | 0328421 A2 | 8/1989 |

(Continued)

OTHER PUBLICATIONS

US 6,503,260, 01/2003, Schaller et al. (withdrawn).

*Primary Examiner* — Melanie Tyson
*Assistant Examiner* — Todd J Scherbel

(57) ABSTRACT

This invention generally relates to devices and methods for repairing an aperture in biological tissue. In certain embodiments the invention provides as system for closing an aperture in a biological tissue including a handle, an elongate shaft connected to the handle, a deployment scaffold connected to the shaft, in which the scaffold is configured to releasably retain a surgical implant, and at least one adhesive dispensing system.

27 Claims, 20 Drawing Sheets

(56) References Cited

U.S. PATENT DOCUMENTS

| | | |
|---|---|---|
| 5,176,692 A | 1/1993 | Wilk et al. |
| 5,203,864 A | 4/1993 | Phillips |
| 5,219,077 A | 6/1993 | Transue |
| 5,249,682 A | 10/1993 | Transue |
| 5,254,133 A | 10/1993 | Seid |
| 5,258,000 A | 11/1993 | Gianturco |
| 5,263,969 A | 11/1993 | Phillips |
| 5,289,963 A | 3/1994 | McGarry et al. |
| 5,290,217 A | 3/1994 | Campos |
| 5,292,328 A | 3/1994 | Hain et al. |
| 5,304,187 A | 4/1994 | Green et al. |
| 5,333,624 A | 8/1994 | Tovey |
| 5,354,292 A | 10/1994 | Braeuer et al. |
| 5,356,064 A | 10/1994 | Green et al. |
| 5,356,432 A | 10/1994 | Rutkow et al. |
| 5,364,002 A | 11/1994 | Green et al. |
| 5,364,004 A | 11/1994 | Davidson |
| 5,366,460 A | 11/1994 | Eberbach |
| 5,368,602 A | 11/1994 | de la Torre |
| 5,370,650 A | 12/1994 | Tovey et al. |
| 5,376,097 A | 12/1994 | Phillips |
| 5,383,477 A | 1/1995 | DeMatteis |
| 5,392,978 A | 2/1995 | Velez et al. |
| 5,397,331 A | 3/1995 | Himpens et al. |
| 5,405,360 A | 4/1995 | Tovey |
| 5,425,357 A | 6/1995 | Moll et al. |
| 5,425,740 A | 6/1995 | Hutchinson |
| 5,433,996 A | 7/1995 | Kranzler et al. |
| 5,464,403 A | 11/1995 | Kieturakis et al. |
| 5,497,933 A | 3/1996 | Defonzo et al. |
| 5,531,759 A | 7/1996 | Kensey et al. |
| 5,560,224 A | 10/1996 | Tessler |
| 5,560,532 A | 10/1996 | DeFonzo et al. |
| 5,564,615 A | 10/1996 | Bishop et al. |
| 5,569,273 A | 10/1996 | Titone et al. |
| 5,577,654 A | 11/1996 | Bishop |
| 5,588,580 A | 12/1996 | Paul et al. |
| 5,588,581 A | 12/1996 | Conlon et al. |
| 5,601,224 A | 2/1997 | Bishop et al. |
| 5,614,284 A | 3/1997 | Kranzler et al. |
| 5,618,290 A | 4/1997 | Toy et al. |
| 5,626,587 A | 5/1997 | Bishop et al. |
| 5,634,584 A | 6/1997 | Okorocha et al. |
| 5,634,931 A | 6/1997 | Kugel |
| 5,662,662 A | 9/1997 | Bishop et al. |
| 5,695,525 A | 12/1997 | Mulhauser et al. |
| 5,716,409 A | 2/1998 | Debbas |
| 5,725,577 A | 3/1998 | Saxon |
| 5,728,119 A | 3/1998 | Smith et al. |
| 5,749,895 A | 5/1998 | Sawyer et al. |
| 5,749,968 A * | 5/1998 | Melanson et al. ............. 118/300 |
| 5,766,246 A | 6/1998 | Mulhauser et al. |
| 5,769,864 A | 6/1998 | Kugel |
| 5,779,728 A | 7/1998 | Lunsford et al. |
| 5,810,851 A | 9/1998 | Yoon |
| 5,814,058 A | 9/1998 | Carlson et al. |
| 5,817,109 A | 10/1998 | McGarry et al. |
| 5,824,082 A | 10/1998 | Brown |
| 5,836,961 A | 11/1998 | Kieturakis et al. |
| 5,854,383 A | 12/1998 | Erneta et al. |
| 5,863,531 A | 1/1999 | Naughton et al. |
| 5,865,728 A | 2/1999 | Moll et al. |
| 5,911,726 A | 6/1999 | Belknap |
| 5,916,225 A | 6/1999 | Kugel |
| 5,925,058 A | 7/1999 | Smith et al. |
| 5,951,997 A | 9/1999 | Bezwada et al. |
| 5,954,767 A | 9/1999 | Pajotin et al. |
| 5,972,007 A | 10/1999 | Sheffield et al. |
| 5,972,008 A | 10/1999 | Kalinski et al. |
| 5,990,378 A | 11/1999 | Ellis |
| 6,004,333 A | 12/1999 | Sheffield et al. |
| 6,042,592 A | 3/2000 | Schmitt |
| 6,066,776 A | 5/2000 | Goodwin et al. |
| 6,066,777 A | 5/2000 | Benchetrit |
| 6,090,116 A | 7/2000 | D'Aversa et al. |
| 6,113,609 A | 9/2000 | Adams |
| 6,113,611 A | 9/2000 | Allen et al. |
| 6,113,624 A | 9/2000 | Bezwada et al. |
| 6,166,286 A | 12/2000 | Trabucco |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,197,036 B1 | 3/2001 | Tripp et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,113 B1 | 7/2001 | Adams et al. |
| 6,258,124 B1 | 7/2001 | Darois et al. |
| 6,267,772 B1 | 7/2001 | Mulhauser et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,312,442 B1 | 11/2001 | Kieturakis et al. |
| 6,319,264 B1 | 11/2001 | Tormala et al. |
| 6,368,541 B1 | 4/2002 | Pajotin et al. |
| 6,375,662 B1 | 4/2002 | Schmitt |
| 6,383,201 B1 | 5/2002 | Dong |
| 6,391,060 B1 | 5/2002 | Ory et al. |
| 6,394,982 B1 * | 5/2002 | Ehrenfels ..................... 604/191 |
| 6,408,656 B1 | 6/2002 | Ory et al. |
| 6,416,486 B1 | 7/2002 | Wampler |
| 6,416,506 B1 * | 7/2002 | Tilton et al. ..................... 606/1 |
| 6,425,900 B1 | 7/2002 | Knodel et al. |
| 6,425,924 B1 | 7/2002 | Rousseau |
| 6,436,030 B2 | 8/2002 | Rehil |
| 6,447,524 B1 | 9/2002 | Knodel et al. |
| 6,478,803 B1 | 11/2002 | Kapec et al. |
| 6,485,503 B2 | 11/2002 | Jacobs et al. |
| 6,497,650 B1 | 12/2002 | Nicolo |
| 6,517,584 B1 | 2/2003 | Lecalve |
| 6,527,785 B2 | 3/2003 | Sancoff et al. |
| 6,547,467 B2 * | 4/2003 | Quintero ..................... 401/132 |
| 6,551,241 B1 | 4/2003 | Schultz |
| 6,551,333 B2 | 4/2003 | Kuhns et al. |
| 6,558,400 B2 | 5/2003 | Deem et al. |
| 6,565,590 B2 | 5/2003 | Kieturakis et al. |
| 6,575,988 B2 | 6/2003 | Rousseau |
| 6,607,541 B1 | 8/2003 | Gardiner et al. |
| 6,610,006 B1 | 8/2003 | Amid et al. |
| 6,613,059 B2 | 9/2003 | Schaller et al. |
| 6,616,685 B2 | 9/2003 | Rousseau |
| 6,638,208 B1 | 10/2003 | Natarajan et al. |
| 6,638,284 B1 | 10/2003 | Rousseau et al. |
| 6,638,292 B2 | 10/2003 | Adams |
| 6,638,297 B1 | 10/2003 | Huitema |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,676,643 B2 | 1/2004 | Brushey |
| 6,689,047 B2 | 2/2004 | Gellman |
| 6,694,192 B2 | 2/2004 | Policker et al. |
| 6,695,856 B2 | 2/2004 | Kieturakis et al. |
| 6,709,442 B2 | 3/2004 | Miller et al. |
| 6,736,823 B2 | 5/2004 | Darois et al. |
| 6,736,854 B2 | 5/2004 | Vadurro et al. |
| 6,746,458 B1 | 6/2004 | Cloud |
| 6,755,867 B2 | 6/2004 | Rousseau |
| 6,773,438 B1 | 8/2004 | Knodel et al. |
| 6,783,554 B2 | 8/2004 | Amara et al. |
| 6,790,213 B2 | 9/2004 | Cherok et al. |
| 6,800,081 B2 | 10/2004 | Parodi |
| 6,800,082 B2 | 10/2004 | Rousseau |
| 6,805,669 B2 | 10/2004 | Swanbom |
| 6,833,408 B2 | 12/2004 | Sehl et al. |
| 6,837,893 B2 | 1/2005 | Miller |
| 6,893,452 B2 | 5/2005 | Jacobs |
| 6,913,607 B2 | 7/2005 | Ainsworth et al. |
| 6,913,622 B2 | 7/2005 | Gjunter |
| 6,936,052 B2 | 8/2005 | Gellman et al. |
| 6,945,980 B2 | 9/2005 | Nguyen et al. |
| 6,953,428 B2 | 10/2005 | Gellman et al. |
| 6,960,217 B2 | 11/2005 | Bolduc |
| 6,960,233 B1 | 11/2005 | Berg et al. |

(56) References Cited

U.S. PATENT DOCUMENTS

| | | |
|---|---|---|
| 6,966,916 B2 | 11/2005 | Kumar |
| 6,974,586 B2 | 12/2005 | Greenhalgh et al. |
| 6,991,597 B2 | 1/2006 | Gellman et al. |
| 7,001,405 B2 | 2/2006 | Kieturakis et al. |
| 7,011,688 B2 | 3/2006 | Gryska et al. |
| 7,025,772 B2 | 4/2006 | Gellman et al. |
| 7,049,345 B2 | 5/2006 | Holmes-Farley |
| 7,077,850 B2 | 7/2006 | Kortenbach |
| 7,083,629 B2 | 8/2006 | Weller et al. |
| 7,083,630 B2 | 8/2006 | DeVries et al. |
| 7,094,261 B2 | 8/2006 | Zotti et al. |
| 7,101,366 B2 | 9/2006 | Trout, III et al. |
| 7,101,381 B2 | 9/2006 | Ford et al. |
| 7,119,062 B1 | 10/2006 | Alvis et al. |
| 7,148,315 B2 | 12/2006 | Erneta et al. |
| 7,198,046 B1 | 4/2007 | Argenta et al. |
| 7,214,236 B2 | 5/2007 | Kieturakis et al. |
| 7,216,651 B2 | 5/2007 | Argenta et al. |
| 7,220,282 B2 | 5/2007 | Kuslich |
| 7,229,452 B2 | 6/2007 | Kayan |
| 7,235,043 B2 | 6/2007 | Gellman et al. |
| 7,235,295 B2 | 6/2007 | Laurencin et al. |
| 7,255,675 B2 | 8/2007 | Gertner et al. |
| 7,320,325 B2 | 1/2008 | Duchon et al. |
| 7,331,199 B2 | 2/2008 | Ory et al. |
| 7,381,225 B2 | 6/2008 | Croce et al. |
| 7,404,819 B1 | 7/2008 | Darios et al. |
| 7,406,969 B2 | 8/2008 | Duchon et al. |
| 7,407,480 B2 | 8/2008 | Staskin et al. |
| 7,491,232 B2 | 2/2009 | Bolduc et al. |
| 7,500,945 B2 | 3/2009 | Cox et al. |
| 7,500,993 B2 | 3/2009 | De La Torre et al. |
| 7,524,333 B2 | 4/2009 | Lambrecht et al. |
| 7,544,213 B2 | 6/2009 | Adams |
| 7,553,329 B2 | 6/2009 | Lambrecht et al. |
| 7,553,330 B2 | 6/2009 | Lambrecht et al. |
| RE40,833 E | 7/2009 | Wintermantel et al. |
| 7,566,337 B2 | 7/2009 | Sogaard-Andersen et al. |
| 7,594,921 B2 | 9/2009 | Browning |
| 7,601,118 B2 | 10/2009 | Smith et al. |
| 7,601,172 B2 | 10/2009 | Segal et al. |
| 7,678,133 B2 * | 3/2010 | Modesitt ..................... 606/216 |
| 7,946,453 B2 * | 5/2011 | Voegele et al. ............... 222/134 |
| 2001/0016754 A1 | 8/2001 | Adams et al. |
| 2001/0018592 A1 | 8/2001 | Schaller et al. |
| 2001/0018593 A1 | 8/2001 | Nguyen et al. |
| 2001/0044637 A1 | 11/2001 | Jacobs et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2001/0056275 A1 | 12/2001 | Brushey |
| 2002/0010457 A1 | 1/2002 | Duchon et al. |
| 2002/0010480 A1 | 1/2002 | Sancoff et al. |
| 2002/0010490 A1 | 1/2002 | Schaller et al. |
| 2002/0010494 A1 | 1/2002 | Policker et al. |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0058967 A1 | 5/2002 | Jervis |
| 2002/0065524 A1 | 5/2002 | Miller et al. |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rousseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078603 A1 | 4/2003 | Schaller et al. |
| 2003/0105473 A1 | 6/2003 | Miller |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0010317 A1 | 1/2004 | Lambrecht et al. |
| 2004/0019360 A1 | 1/2004 | Farnsworth et al. |
| 2004/0024386 A1 | 2/2004 | Deem et al. |
| 2004/0024465 A1 | 2/2004 | Lambrecht et al. |
| 2004/0030217 A1 | 2/2004 | Yeung et al. |
| 2004/0044364 A1 | 3/2004 | DeVries et al. |
| 2004/0044412 A1 | 3/2004 | Lambrecht et al. |
| 2004/0049227 A1 | 3/2004 | Jervis |
| 2004/0049282 A1 | 3/2004 | Gjunter |
| 2004/0054376 A1 | 3/2004 | Ory et al. |
| 2004/0059356 A1 | 3/2004 | Gingras |
| 2004/0064131 A1 | 4/2004 | Brushey |
| 2004/0073237 A1 | 4/2004 | Leinsing |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097924 A1 | 5/2004 | Lambrecht et al. |
| 2004/0097986 A1 | 5/2004 | Adams |
| 2004/0122452 A1 | 6/2004 | Deem et al. |
| 2004/0122453 A1 | 6/2004 | Deem et al. |
| 2004/0133214 A1 | 7/2004 | Kayan |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0249412 A1 | 12/2004 | Snow et al. |
| 2004/0254592 A1 | 12/2004 | DiCarlo et al. |
| 2005/0010239 A1 | 1/2005 | Chefitz |
| 2005/0010306 A1 | 1/2005 | Priewe et al. |
| 2005/0015102 A1 | 1/2005 | Chefitz |
| 2005/0019436 A1 | 1/2005 | Burch et al. |
| 2005/0021058 A1 | 1/2005 | Negro |
| 2005/0033318 A1 | 2/2005 | Miller et al. |
| 2005/0038452 A1 | 2/2005 | Chu |
| 2005/0054771 A1 | 3/2005 | Sehl et al. |
| 2005/0055097 A1 | 3/2005 | Grunberg et al. |
| 2005/0060038 A1 | 3/2005 | Lambrecht et al. |
| 2005/0065072 A1 | 3/2005 | Keeler et al. |
| 2005/0075667 A1 | 4/2005 | Schaller et al. |
| 2005/0080454 A1 | 4/2005 | Drews et al. |
| 2005/0113849 A1 | 5/2005 | Popadiuk et al. |
| 2005/0113858 A1 | 5/2005 | Deutsch |
| 2005/0118239 A1 | 6/2005 | Sabesan |

(56) References Cited

U.S. PATENT DOCUMENTS

| | | |
|---|---|---|
| 2005/0129733 A1 | 6/2005 | Milbocker et al. |
| 2005/0142315 A1 | 6/2005 | DeSimone et al. |
| 2005/0143817 A1 | 6/2005 | Hunter et al. |
| 2005/0149072 A1 | 7/2005 | DeVries et al. |
| 2005/0149080 A1 | 7/2005 | Hunter et al. |
| 2005/0149158 A1 | 7/2005 | Hunter et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0165488 A1 | 7/2005 | Hunter et al. |
| 2005/0169959 A1 | 8/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0192600 A1 | 9/2005 | Nicolo et al. |
| 2005/0202067 A1 | 9/2005 | Lendlein et al. |
| 2005/0222591 A1 | 10/2005 | Gingras et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0245787 A1 | 11/2005 | Cox et al. |
| 2005/0249770 A1 | 11/2005 | Hunter |
| 2005/0267325 A1 | 12/2005 | Bouchier et al. |
| 2005/0271794 A1 | 12/2005 | DeSimone et al. |
| 2005/0273146 A1 | 12/2005 | DeSimone et al. |
| 2005/0283189 A1 | 12/2005 | Rosenblatt |
| 2005/0283190 A1 | 12/2005 | Huitema et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1* | 1/2006 | Modesitt ............... 606/215 |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0047180 A1 | 3/2006 | Hegde et al. |
| 2006/0052816 A1 | 3/2006 | Bates et al. |
| 2006/0064175 A1 | 3/2006 | Pelissier et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller et al. |
| 2006/0147492 A1 | 7/2006 | Hunter et al. |
| 2006/0149316 A1 | 7/2006 | DeVries et al. |
| 2006/0155165 A1* | 7/2006 | Vanden Hoek et al. ......... 600/37 |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0200246 A1 | 9/2006 | Lambrecht et al. |
| 2006/0206178 A1 | 9/2006 | Kim |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0253203 A1 | 11/2006 | Alvarado |
| 2006/0264698 A1 | 11/2006 | Kondonis et al. |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2007/0016300 A1 | 1/2007 | Kuslich |
| 2007/0021756 A1 | 1/2007 | Kortenbach |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0038310 A1 | 2/2007 | Guetty |
| 2007/0100355 A1 | 5/2007 | Bonde et al. |
| 2007/0110786 A1 | 5/2007 | Tenney et al. |
| 2007/0111937 A1 | 5/2007 | Pickar et al. |
| 2007/0118133 A1 | 5/2007 | Lambrecht et al. |
| 2007/0118158 A1 | 5/2007 | Deem et al. |
| 2007/0118159 A1 | 5/2007 | Deem et al. |
| 2007/0122425 A1 | 5/2007 | Keeler et al. |
| 2007/0135929 A1 | 6/2007 | Williams et al. |
| 2007/0156245 A1 | 7/2007 | Cauthen et al. |
| 2007/0162135 A1 | 7/2007 | Segal et al. |
| 2007/0167963 A1 | 7/2007 | Deem et al. |
| 2007/0173864 A1 | 7/2007 | Chu |
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1 | 8/2007 | Jackson |
| 2007/0185541 A1 | 8/2007 | DiUbaldi et al. |
| 2007/0198040 A1 | 8/2007 | Buevich et al. |
| 2007/0202148 A1 | 8/2007 | Ringeisen et al. |
| 2007/0202173 A1 | 8/2007 | Cueto-Garcia |
| 2007/0203507 A1 | 8/2007 | McLaughlin et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0299300 A1 | 12/2007 | Smith et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0091222 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0167667 A1 | 7/2008 | Criscuolo et al. |
| 2008/0167668 A1 | 7/2008 | Criscuolo et al. |
| 2008/0188874 A1 | 8/2008 | Henderson |
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0243149 A1 | 10/2008 | Kockerling et al. |
| 2008/0269896 A1 | 10/2008 | Cherok et al. |
| 2008/0281433 A1 | 11/2008 | Chang et al. |
| 2008/0287970 A1 | 11/2008 | Amato et al. |
| 2008/0312751 A1 | 12/2008 | Pugsley et al. |
| 2009/0004239 A1 | 1/2009 | Ladet et al. |
| 2009/0012350 A1 | 1/2009 | Tihon |
| 2009/0012546 A1 | 1/2009 | N'diaye et al. |
| 2009/0030434 A1 | 1/2009 | Paz et al. |
| 2009/0030522 A1 | 1/2009 | Cauthen, III et al. |
| 2009/0030527 A1 | 1/2009 | Richter |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0062823 A1 | 3/2009 | Richter |
| 2009/0069826 A1 | 3/2009 | Walther et al. |
| 2009/0099579 A1* | 4/2009 | Nentwick et al. ............. 606/151 |
| 2009/0105526 A1 | 4/2009 | Piroli Torelli et al. |
| 2009/0125041 A1 | 5/2009 | Dudai |
| 2009/0137864 A1 | 5/2009 | Cox et al. |
| 2009/0155332 A1 | 6/2009 | Sherry et al. |
| 2009/0157184 A1 | 6/2009 | Cauthen, III et al. |
| 2009/0157195 A1 | 6/2009 | Siedle |
| 2009/0182190 A1 | 7/2009 | Dann |
| 2009/0182352 A1 | 7/2009 | Paz et al. |
| 2009/0187258 A1 | 7/2009 | Ip et al. |
| 2009/0192346 A1 | 7/2009 | Rosenblatt |

(56) References Cited

U.S. PATENT DOCUMENTS

| | | |
|---|---|---|
| 2009/0198260 A1 | 8/2009 | Ford et al. |
| 2009/0204130 A1 | 8/2009 | Kantsevoy et al. |
| 2009/0204227 A1 | 8/2009 | Derwin et al. |
| 2009/0216075 A1 | 8/2009 | Bell et al. |
| 2009/0216104 A1 | 8/2009 | Desimone et al. |
| 2009/0234379 A1 | 9/2009 | Rehnke |
| 2009/0248048 A1 | 10/2009 | Milbocker |
| 2009/0254103 A1 | 10/2009 | Deutsch |
| 2009/0259094 A1 | 10/2009 | Bouchier et al. |
| 2009/0281563 A1 | 11/2009 | Newell et al. |
| 2009/0312843 A1* | 12/2009 | Ford et al. ............... 623/23.72 |
| 2010/0069930 A1 | 3/2010 | Roslin et al. |

FOREIGN PATENT DOCUMENTS

| | | |
|---|---|---|
| EP | 0525791 A1 | 2/1993 |
| EP | 0544485 A1 | 6/1993 |
| EP | 0557963 A1 | 9/1993 |
| EP | 0557964 A1 | 9/1993 |
| EP | 0579377 A2 | 1/1994 |
| EP | 0581036 A1 | 2/1994 |
| EP | 0614650 A2 | 9/1994 |
| EP | 0702934 A1 | 3/1996 |
| EP | 0581036 | 1/1997 |
| EP | 0746258 B1 | 9/1998 |
| EP | 0898944 A2 | 3/1999 |
| EP | 0908482 A1 | 4/1999 |
| EP | 1060714 A2 | 12/2000 |
| EP | 1181899 A2 | 2/2002 |
| EP | 1199037 A2 | 4/2002 |
| EP | 1199038 A2 | 4/2002 |
| EP | 1219265 A2 | 7/2002 |
| EP | 1018980 B1 | 1/2003 |
| EP | 1306061 A2 | 5/2003 |
| EP | 1317904 A1 | 6/2003 |
| EP | 1366717 A1 | 12/2003 |
| EP | 1200010 B1 | 3/2005 |
| EP | 1164967 B1 | 5/2005 |
| EP | WO2005082273 A1 | 9/2005 |
| EP | 0828453 B1 | 11/2005 |
| EP | 1607048 A1 | 12/2005 |
| EP | 1404250 B1 | 2/2006 |
| EP | 1671604 A2 | 6/2006 |
| EP | 1274473 B1 | 7/2006 |
| EP | 0934024 B1 | 8/2006 |
| EP | 1503683 B1 | 8/2006 |
| EP | 1700579 A1 | 9/2006 |
| EP | 1704832 A2 | 9/2006 |
| EP | 200614650 A2 | 10/2006 |
| EP | 1079741 B1 | 11/2006 |
| EP | 0964645 B1 | 7/2007 |
| EP | 1163019 B1 | 10/2007 |
| EP | 1849440 A1 | 10/2007 |
| EP | 1867348 A2 | 12/2007 |
| EP | 1531739 B1 | 2/2008 |
| EP | 1406557 B1 | 11/2008 |
| EP | 1990014 A2 | 11/2008 |
| EP | 2002800 A1 | 12/2008 |
| EP | 1505927 B1 | 1/2009 |
| EP | 1372525 B1 | 3/2009 |
| EP | 1653880 B1 | 4/2009 |
| EP | 2050474 A2 | 4/2009 |
| EP | 1940312 B1 | 7/2009 |
| FR | 2789888 | 8/2000 |
| FR | 2789888 A1 | 8/2000 |
| WO | WO8204390 A1 | 12/1982 |
| WO | WO92/06639 | 4/1992 |
| WO | WO9206639 A2 | 4/1992 |
| WO | WO9211824 A1 | 7/1992 |
| WO | WO9219162 A2 | 11/1992 |
| WO | WO9221293 A1 | 12/1992 |
| WO | WO9309722 A1 | 5/1993 |
| WO | WO9317635 A1 | 9/1993 |
| WO | WO9417747 A1 | 8/1994 |
| WO | WO9419029 A1 | 9/1994 |
| WO | WO94/27535 | 12/1994 |
| WO | WO9427535 A1 | 12/1994 |
| WO | WO9530374 A1 | 11/1995 |
| WO | WO9531140 A1 | 11/1995 |
| WO | WO9603165 A1 | 2/1996 |
| WO | WO9606634 A1 | 3/1996 |
| WO | WO9609795 A1 | 4/1996 |
| WO | WO9722371 A1 | 6/1997 |
| WO | WO9732526 A1 | 9/1997 |
| WO | WO9735533 A1 | 10/1997 |
| WO | WO9803713 A1 | 1/1998 |
| WO | WO9811814 | 3/1998 |
| WO | WO9814134 A2 | 4/1998 |
| WO | WO9905992 A1 | 2/1999 |
| WO | WO9916381 A1 | 4/1999 |
| WO | WO9951163 A1 | 10/1999 |
| WO | WO9960931 A1 | 12/1999 |
| WO | WO9962406 A2 | 12/1999 |
| WO | WO9963051 A2 | 12/1999 |
| WO | WO0007520 A1 | 2/2000 |
| WO | WO0016822 A2 | 3/2000 |
| WO | WO0056376 A1 | 9/2000 |
| WO | WO0057796 A1 | 10/2000 |
| WO | WO0057812 A1 | 10/2000 |
| WO | WO0061033 | 10/2000 |
| WO | WO0067663 A1 | 11/2000 |
| WO | WO0071548 A1 | 11/2000 |
| WO | WO0071549 A1 | 11/2000 |
| WO | WO0108594 A1 | 2/2001 |
| WO | WO0126588 A2 | 4/2001 |
| WO | WO0154589 A1 | 8/2001 |
| WO | WO0168653 A1 | 9/2001 |
| WO | WO0170322 A1 | 9/2001 |
| WO | WO0180788 A2 | 11/2001 |
| WO | WO0185058 A2 | 11/2001 |
| WO | WO0185060 | 11/2001 |
| WO | WO0189392 A2 | 11/2001 |
| WO | WO0217771 A2 | 3/2002 |
| WO | WO0217796 A1 | 3/2002 |
| WO | WO0217797 A1 | 3/2002 |
| WO | WO0219916 A1 | 3/2002 |
| WO | WO0219923 A1 | 3/2002 |
| WO | WO0222047 A1 | 3/2002 |
| WO | WO0224080 A2 | 3/2002 |
| WO | WO0226747 A1 | 4/2002 |
| WO | WO0230336 A2 | 4/2002 |
| WO | WO0234140 A1 | 5/2002 |
| WO | WO0235990 A2 | 5/2002 |
| WO | WO02058543 A2 | 8/2002 |
| WO | WO02078568 A1 | 10/2002 |
| WO | WO02080779 A1 | 10/2002 |
| WO | WO02080780 A1 | 10/2002 |
| WO | WO02/091953 | 11/2002 |
| WO | WO02087425 A2 | 11/2002 |
| WO | WO02091928 A1 | 11/2002 |
| WO | WO02091953 A1 | 11/2002 |
| WO | WO02096327 A2 | 12/2002 |
| WO | WO03002130 A1 | 1/2003 |
| WO | WO03032867 A1 | 4/2003 |
| WO | WO03059180 A2 | 7/2003 |
| WO | WO03059201 A1 | 7/2003 |
| WO | WO03059217 A1 | 7/2003 |
| WO | WO03077730 A2 | 9/2003 |
| WO | WO03082125 A1 | 10/2003 |
| WO | WO03084410 A1 | 10/2003 |
| WO | WO03088846 A1 | 10/2003 |
| WO | WO03090633 A2 | 11/2003 |
| WO | WO03092509 A1 | 11/2003 |
| WO | WO03094781 A1 | 11/2003 |
| WO | WO03094783 A1 | 11/2003 |
| WO | WO03094786 A1 | 11/2003 |
| WO | WO03094787 A1 | 11/2003 |
| WO | WO03096909 A1 | 11/2003 |
| WO | WO03097011 A1 | 11/2003 |
| WO | WO03099160 A1 | 12/2003 |
| WO | WO03103473 A2 | 12/2003 |
| WO | WO2004004600 A1 | 1/2004 |
| WO | WO2004012579 A2 | 2/2004 |

(56) References Cited

FOREIGN PATENT DOCUMENTS

| | | |
|---|---|---|
| WO | WO2004012627 A1 | 2/2004 |
| WO | WO2004019787 A2 | 3/2004 |
| WO | WO2004034924 A2 | 4/2004 |
| WO | WO2004/062529 | 7/2004 |
| WO | WO2004058286 A1 | 7/2004 |
| WO | WO2004060425 A2 | 7/2004 |
| WO | WO2004062529 A2 | 7/2004 |
| WO | WO2004028547 A1 | 8/2004 |
| WO | WO2004069866 A1 | 8/2004 |
| WO | WO2004/080348 | 9/2004 |
| WO | WO2004080348 A1 | 9/2004 |
| WO | WO2004087227 A1 | 10/2004 |
| WO | WO2004093737 A1 | 11/2004 |
| WO | WO2004098665 A1 | 11/2004 |
| WO | WO2004100841 A1 | 11/2004 |
| WO | WO2004101002 A2 | 11/2004 |
| WO | WO2004103166 A2 | 12/2004 |
| WO | WO2004103414 A2 | 12/2004 |
| WO | WO2005003351 A1 | 1/2005 |
| WO | WO2005004727 A1 | 1/2005 |
| WO | WO2005007209 A1 | 1/2005 |
| WO | WO2005014634 A1 | 2/2005 |
| WO | WO2005018494 A1 | 3/2005 |
| WO | WO2005019241 A2 | 3/2005 |
| WO | WO2005019315 A1 | 3/2005 |
| WO | WO2005035548 A1 | 4/2005 |
| WO | WO2005041784 A2 | 5/2005 |
| WO | WO2005044143 A1 | 5/2005 |
| WO | WO2005051172 A2 | 6/2005 |
| WO | WO2005055958 A2 | 6/2005 |
| WO | WO2005065324 A2 | 7/2005 |
| WO | WO2005065552 A2 | 7/2005 |
| WO | WO2005079335 A2 | 9/2005 |
| WO | WO2005099628 A2 | 10/2005 |
| WO | WO2005102209 A1 | 11/2005 |
| WO | WO2005110243 A2 | 11/2005 |
| WO | WO2005110273 A1 | 11/2005 |
| WO | WO2006002439 A1 | 1/2006 |
| WO | WO2006008429 A1 | 1/2006 |
| WO | WO2006012353 A2 | 2/2006 |
| WO | WO2006013337 A2 | 2/2006 |
| WO | WO2006015031 A2 | 2/2006 |
| WO | WO2006026509 A2 | 3/2006 |
| WO | WO2006034117 A1 | 3/2006 |
| WO | WO2006036936 A2 | 4/2006 |
| WO | WO2006037047 A2 | 4/2006 |
| WO | WO2006040760 A2 | 4/2006 |
| WO | WO2006044785 A1 | 4/2006 |
| WO | WO2006047645 A2 | 5/2006 |
| WO | WO2006048885 A1 | 5/2006 |
| WO | WO2006082587 A2 | 8/2006 |
| WO | WO2006086339 A2 | 8/2006 |
| WO | WO2006092159 A1 | 9/2006 |
| WO | WO2006092236 A1 | 9/2006 |
| WO | WO2006102457 A2 | 9/2006 |
| WO | WO2006116000 A2 | 11/2006 |
| WO | WO2006119034 A2 | 11/2006 |
| WO | WO2007004228 A1 | 1/2007 |
| WO | WO2007011689 A2 | 1/2007 |
| WO | WO2007017872 A2 | 2/2007 |
| WO | WO2007021620 A2 | 2/2007 |
| WO | WO2007021834 A1 | 2/2007 |
| WO | WO2007/025302 | 3/2007 |
| WO | WO/2007/030676 | 3/2007 |
| WO | WO2007025293 A2 | 3/2007 |
| WO | WO2007025296 A2 | 3/2007 |
| WO | WO2007025302 A2 | 3/2007 |
| WO | WO2007030676 A2 | 3/2007 |
| WO | WO2007034145 A2 | 3/2007 |
| WO | WO2007055755 A1 | 5/2007 |
| WO | WO2007072469 A2 | 6/2007 |
| WO | WO2007081955 A1 | 7/2007 |
| WO | WO2007087132 A1 | 8/2007 |
| WO | WO2007087146 A2 | 8/2007 |
| WO | WO2007115110 A2 | 10/2007 |
| WO | WO2007129220 A2 | 11/2007 |
| WO | WO2007133311 A2 | 11/2007 |
| WO | WO2007136820 A2 | 11/2007 |
| WO | WO2007137211 A2 | 11/2007 |
| WO | WO2007143726 A2 | 12/2007 |
| WO | WO2007144782 A2 | 12/2007 |
| WO | WO2007146784 A2 | 12/2007 |
| WO | WO2008006097 A2 | 1/2008 |
| WO | WO2008016802 A1 | 2/2008 |
| WO | WO2008026905 A2 | 3/2008 |
| WO | WO2008030939 A2 | 3/2008 |
| WO | WO2008/045635 | 4/2008 |
| WO | WO2008045635 A2 | 4/2008 |
| WO | WO2008/065653 | 6/2008 |
| WO | WO2008065653 A1 | 6/2008 |
| WO | WO2008069919 A2 | 6/2008 |
| WO | WO2008085825 A1 | 7/2008 |
| WO | WO2008/099382 | 8/2008 |
| WO | WO2008094217 A1 | 8/2008 |
| WO | WO2008094842 A1 | 8/2008 |
| WO | WO2008099382 A1 | 8/2008 |
| WO | WO2008112437 A2 | 9/2008 |
| WO | WO2008124056 A1 | 10/2008 |
| WO | WO2008140989 A2 | 11/2008 |
| WO | WO2008157497 A2 | 12/2008 |
| WO | WO2008157777 A1 | 12/2008 |
| WO | WO2009005625 A1 | 1/2009 |
| WO | WO2009005634 A1 | 1/2009 |
| WO | WO2009011824 A1 | 1/2009 |
| WO | WO2009012001 A1 | 1/2009 |
| WO | WO2009022348 A1 | 2/2009 |
| WO | WO2009036094 A2 | 3/2009 |
| WO | WO2009039371 A1 | 3/2009 |
| WO | WO2009/050717 | 4/2009 |
| WO | WO2009042442 A1 | 4/2009 |
| WO | WO2009048314 A1 | 4/2009 |
| WO | WO2009050717 A2 | 4/2009 |
| WO | WO2009059005 A1 | 5/2009 |
| WO | WO2009064845 A2 | 5/2009 |
| WO | WO2009069119 A1 | 6/2009 |
| WO | WO2009075786 A1 | 6/2009 |
| WO | WO2009075932 A1 | 6/2009 |
| WO | WO2009075933 A1 | 6/2009 |
| WO | WO2009086446 A1 | 7/2009 |
| WO | WO2009092294 A1 | 7/2009 |
| WO | WO2009094015 A1 | 7/2009 |
| WO | WO2009/104182 | 8/2009 |
| WO | WO2009097380 A1 | 8/2009 |
| WO | WO2009102792 A2 | 8/2009 |
| WO | WO2009104182 A2 | 8/2009 |
| WO | WO2009113972 A2 | 9/2009 |
| WO | WO2009126781 A1 | 10/2009 |
| WO | 2011/021082 A1 | 2/2011 |

* cited by examiner

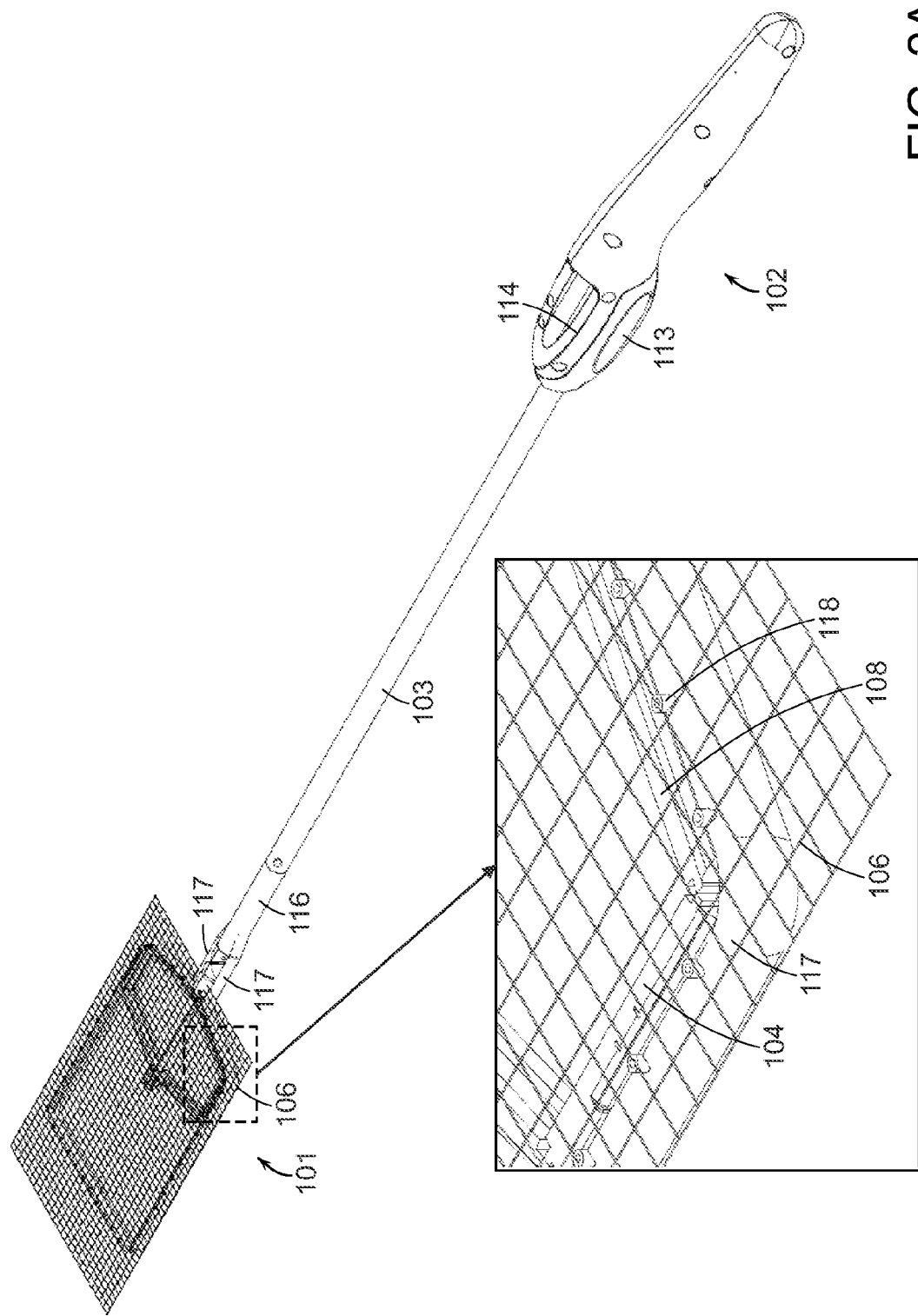
FIG. 2A1

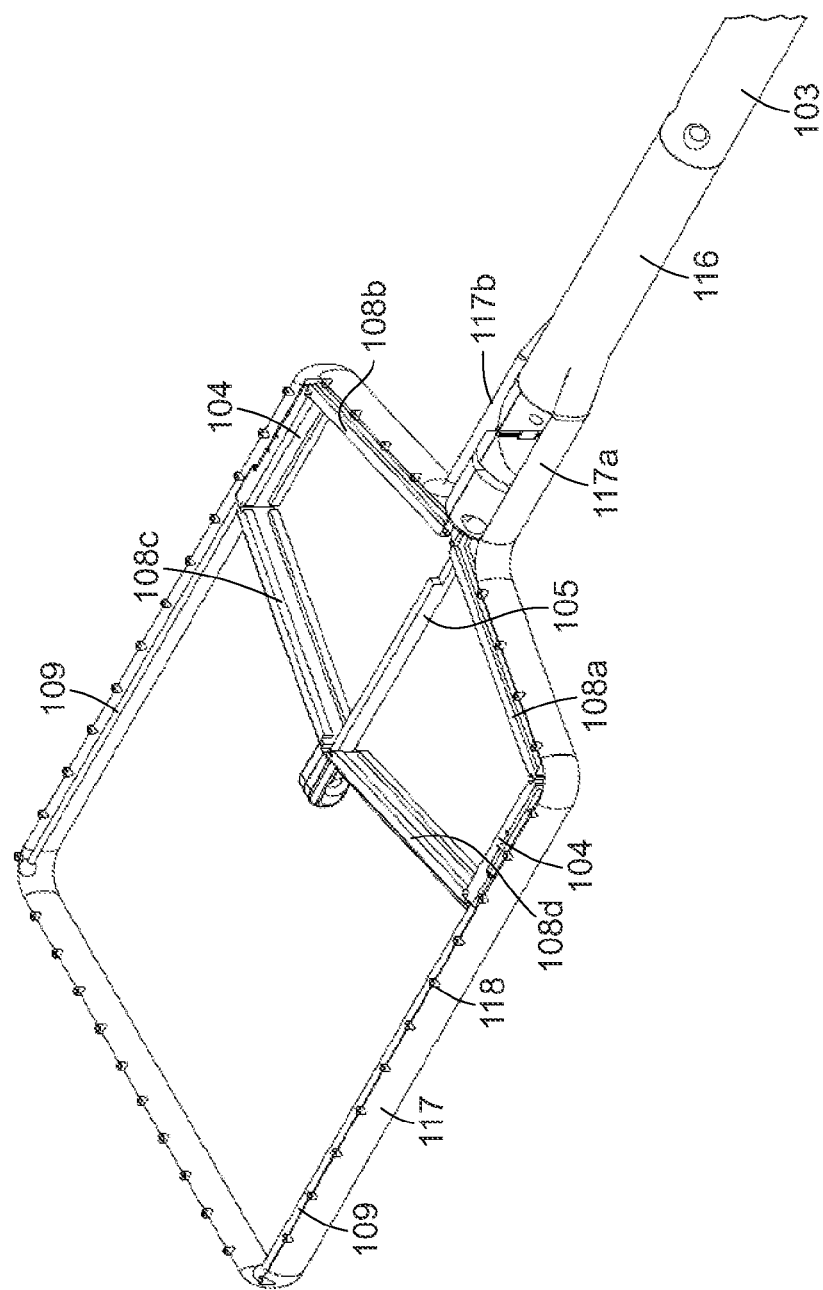
FIG. 2A2

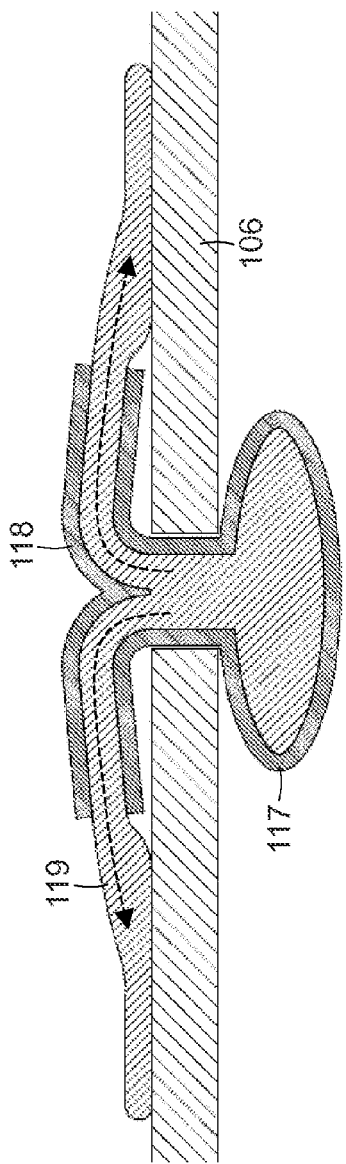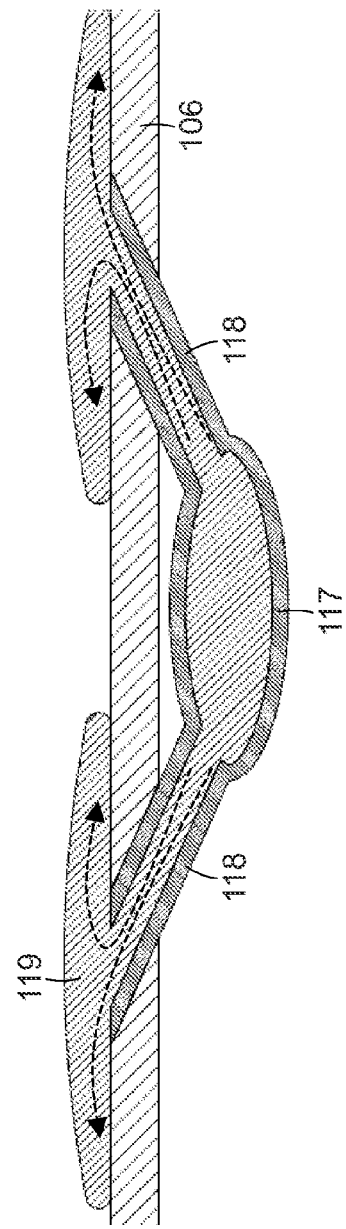

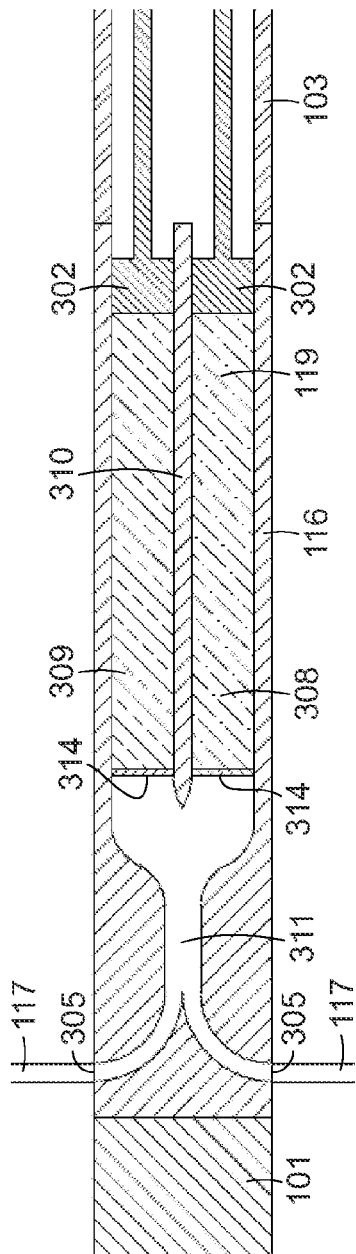
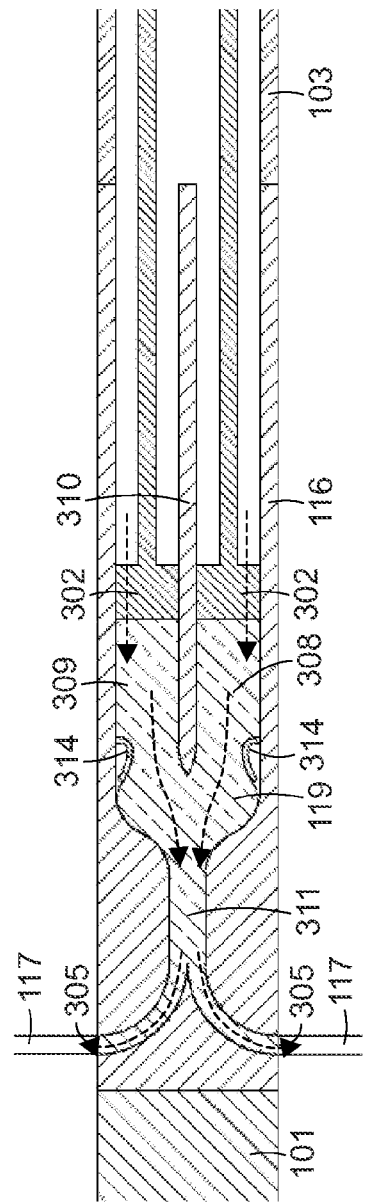
FIG. 4F
FIG. 4G

DEVICE AND METHOD FOR ATTACHING AN IMPLANT TO BIOLOGICAL TISSUE

RELATED APPLICATIONS

The present application is a continuation-in-part of PCT international patent application number PCT/IL2009/000985, filed Oct. 20, 2009, which claims the benefit of and priority to U.S. provisional patent application Ser. No. 61/106,616, filed Oct. 20, 2008, the content of each of which is incorporated by reference herein in its entirety.

FIELD OF THE INVENTION

This invention generally relates to devices and methods for repairing an aperture in biological tissue. More specifically, the present invention relates to devices and methods for attaching an implant to biological tissue, using an adhesive.

BACKGROUND

An object of the present invention is to provide apparatus and a method for performing corrective surgery on internal wounds such as hernia where invasion of the patient's body tissues is minimized and resultant trauma is reduced.

A hernia is a protrusion of a tissue, structure, or part of an organ through the muscular tissue or the membrane by which it is normally contained. In other words a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the patch and then to attach/anchor the patch to the tissue.

There are many patents and patent applications relating to anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body. Most tissue anchors secure the tissue by impaling it with one or more posts or legs that are bent or crimped to lock the tissue into position. Thus, most traditional anchors are rigid or are inflexibly attached to the tissue. For example PCT no. wo07021834 describes an anchor having two curved legs that cross in a single turning direction to form a loop. Those two curved legs are adapted to penetrate tissue in a curved pathway. U.S. Pat. No. 4,485,816 ('816') describes surgical staple made of shape memory alloy. The staple is placed in contact of the tissue and then heated. The heating causes the staple to change its shape thus, penetrating the tissue.

U.S. Pat. No. 6,893,452 ('452) describes a tissue attachment device that facilitates wound healing by holding soft tissue together under improved distribution of tension and with minimal disruption of the wound interface and its nutrient supplies. The device has multiple sites for grasping the tissue using tines or prongs or other generally sharp, projecting points, protruding from a single, supportive backing. One of the embodiments described in '452 is the use of sharp projecting points protruding from the supportive backing in two different angles.

U.S. Pat. No. 6,517,584 ('584) describes a hernia patch which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. No. 5,364,004, U.S. Pat. No. 5,662,662, U.S. Pat. No. 5,634,584, U.S. Pat. No. 5,560,224, U.S. Pat. No. 5,588,581 and in U.S. Pat. No. 5,626,587.

There are a few patent and patent literatures relating to deployment of patches. For example U.S. Pat. No. 5,836,961 ('961) which relates to an apparatus used for developing an anatomic space for laparoscopic hernia repair and a patch for use therewith. The apparatus of patent '961 comprises a tubular introducer member having a bore extending there through. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

Another example for deploying the patch can be found in U.S. Pat. No. 5,370,650 ('650) which relates to an apparatus for positioning surgical implants adjacent to body tissue to facilitate the fastening of the implant to the body tissue. Patent '650 provides an apparatus for positioning surgical implants adjacent to body tissue, comprising an outer tube having a proximal end, a distal end and a longitudinal axis; an inner rod at least partially disposed within the outer tube and slidable along said longitudinal axis. The inner rod has a proximal and a distal end portions. The inner rod distal end portion further comprises articulating means for pivoting at an angle with respect to the longitudinal axis. A looped support member having first and second end portions fixedly secured to said distal end portion of the inner rod; and a surgical implant releasably secured to the looped support member.

More patent literature can be found in U.S. Pat. No. 4,190,042 which discloses a resilient surgical retractor which in an unstressed condition forms a hook-like appendage at the distal end of the retractor.

Another patent literature relates to a perpendicular deployment of the patch. An example of such teaching can be found in U.S. Pat. No. 5,405,360 (see FIG. 6). There are many advantages for the lateral deployment over the perpendicular deployment. One of which is the considerably large amount of articulation that will be needed in order to properly position the patch with respect to the hernia. The other one relates to the fact that the abdominal cavity contains a limited space; hence the use of large patches will be limited.

All those patent and patent application demonstrate attachment means for attaching the patch to the tissue or means for deploying the patch within the body. However none of the literature found relates to a device especially adapted to deploy and attached a patch to a biological tissue.

Thus, there is still a long felt need for a device that can be used for both deploying and attaching a patch to a biological tissue namely via a biological glue.

SUMMARY OF THE INVENTION

It is one object of the present invention to provide a deployment and attachment device (DAD) comprising:
a. deployment mechanism adapted to laterally deploy a patch; and,
b. at least one glue dispensing system (GDS), in communication with said deploying mechanism and said patch, adapted to attach said patch to a biological tissue within a body cavity via a biological glue 119;
wherein said GDS comprising:
  i. at least one glue reservoir (GR) 116 adapted to accommodate glue 119; and,
  ii. at least one glue dispensing tube (GDT) 117, in communication with said GR 116, adapted to homogeneously disperse glue 119 along substantially the entire margins area of said patch.

It is another object of the present invention to provide the DAD as defined above, wherein said DAD is characterize by having a distal portion, adapted to be inserted into a body and a proximal portion, located adjacent to a user; said distal portion and said proximal portion are interconnected along a main longitudinal axis via a tube (103);
said tube (103) having a proximal end (TP) connected to said proximal portion, and a distal end (TD);
said tube (103) is adapted to at least partially accommodate a central shaft (105);
said central shaft (105) is characterized by a proximal end (CSP) accommodated within said tube and a distal end (CSD) protruding out of said TD; said central shaft is adapted to reciprocally move parallel to said main longitudinal axis within said tube;
said GR (116) is in communication with said at least one glue dispensing tube (117);
said distal portion comprises:

(i) at least two frame arms (FA) (104) adapted to be reversibly coupled to said patch;
(ii) at least two proximal deployment arms (pDA) (108a, 108b) hinge-like connected to said TD and to the proximal end of said two FA;
(iii) at least two distal deployment arms (dDA) (108c, 108d) hinge-like connected to said CSD and to the distal end of said two FA;
each of said pDA and dDA (108a, 108b, 108c, 108d) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105);
said FAs (104) are characterized by a closed configuration in which said pDAs and dDAs are in said parallel configuration; and, a deployed configuration at which said pDAs and dDAs are in said substantially perpendicular configuration such that said patch is deployed; said FA are adapted to reversibly transform from said closed configuration to said deployed configuration by (i) said reciprocal movement of said central shaft (105) towards and away from said proximal portion; and, (ii) said transformation of each of said DAs from said parallel configuration to said perpendicular configuration, such that said deployment of said patch is at least partially reversible.

It is another object of the present invention to provide the DAD as defined above, wherein said GR 116 is reversible coupled to said tube 103.

It is another object of the present invention to provide the DAD as defined above, said proximal portion comprising at least one handle located outside said body; said handle adapted to (i) reversibly transform said FA from said closed configuration to said open configuration; (ii) disperse said glue on said patch; and, (iii) lateral articulate said DAD.

It is another object of the present invention to provide the DAD as defined above, wherein said GR 116 is reversible coupled to said handle in said proximal portion.

It is another object of the present invention to provide the DAD as defined above, wherein said GR 116 comprising at least one hook 506 adapted to be reversibly inserted into at least one socket 507 located in said tube 103.

It is another object of the present invention to provide the DAD as defined above, wherein said glue is selected from a group consisting of fibrin sealant (FS), Cyanoacrylate or any other glue suitable for clinical use.

It is another object of the present invention to provide the DAD as defined above, additionally comprising a lateral articulating mechanism adapted to provide lateral articulation to said DAD such that said patch can be properly place with respect to said hernia.

It is another object of the present invention to provide the DAD as defined above, additionally comprising a vertical articulating mechanism adapted to provide vertical articulation to said DAD such that said patch can be properly place with respect to said hernia.

It is another object of the present invention to provide the DAD as defined above, wherein said glue dispensing tube (117) is coupled to at least one selected from a group consisting of FA (104), pDA or dDA or any combination thereof.

It is another object of the present invention to provide the DAD as defined above, wherein said glue dispensing tube (117) is reversibly coupled to said patch (106).

It is another object of the present invention to provide the DAD as defined above, wherein said GDT 117 comprises at least one nozzle 118 adapted to disperse said glue on said patch.

It is another object of the present invention to provide the DAD as defined above, wherein said nozzles 118 are pre inserted through said patch such that at least a portion of said nozzles 118 protrude out of said patch 106.

It is another object of the present invention to provide the DAD as defined above, wherein said patch used is a non-pores patch.

It is another object of the present invention to provide the DAD as defined above, wherein said pre inserted nozzles 118 are adapted to provide attachment between said GDT 117 and said patch 106.

It is another object of the present invention to provide the DAD as defined above, wherein said nozzles 118 comprising at least two openings facing to two opposite directions of said patch.

It is another object of the present invention to provide the DAD as defined above, additionally comprising at least one piston 302 internally coupled to said GR 116; said piston 302 is adapted to reciprocal move along the GR's longitudinal axis such that said glue is extracted from said GR 116 to said GDT 117.

It is another object of the present invention to provide the DAD as defined above, wherein said piston 302 is driven by means selected from a group consisting of pneumatic means, mechanic means, hydraulic means or any combination thereof.

It is another object of the present invention to provide the DAD as defined above, wherein said piston is pneumatically driven via compressed gas.

It is another object of the present invention to provide the DAD as defined above, wherein said GR 116 is adapted to accommodate a multi-component glue.

It is another object of the present invention to provide the DAD as defined above, wherein said GR 116 is divided into at least two sealed sub cavities 308, 309 by at least one partition 310.

It is another object of the present invention to provide the DAD as defined above, wherein each sub cavity 308, 309 is coupled to a single mixing cavity 311.

It is another object of the present invention to provide the DAD as defined above, additionally comprising at least one membrane 314 adapted to prevent any unwanted extraction of said glue components.

It is another object of the present invention to provide the DAD as defined above, wherein said GDT 117 is characterized by an oval cross section so as to reduce the overall cross section area of said distal portion 101 in said 'closed configuration'.

It is another object of the present invention to provide the DAD as defined above, wherein said FA (104) comprises means adapted to at least partially reversibly connect said patch (106) to said FA (104).

It is another object of the present invention to provide the DAD as defined above, wherein said glue reservoir (GR) 116 is separately provided.

It is another object of the present invention to provide a method for deploying and attaching a patch to a biological tissue. The method comprising steps selected inter alia from:
a. obtaining a deployment and attachment device (DAD) comprising:
  i. deployment mechanism adapted to laterally deploy a patch; and,
  ii. at least one glue dispensing system (GDS), in communication with said deploying mechanism and said patch, adapted to attach said patch to a biological tissue within a body cavity via a biological glue 119; said GDS comprising: (a) at least one glue reservoir (GR) 116 accommodating glue 119; and, (b) at least one glue dispensing tube (GDT) 117, in communication with said GR 116;
b. attaching said patch to said DAD;
c. introducing said patch into said body cavity;
d. deploying said patch;
e. homogeneously dispersing glue 119 along substantially the entire margins area of said patch; and,
f. adjacently bringing said patch into contact with said biological tissue, thereby attaching said patch to said biological tissue.

It is another object of the present invention to provide a method for deploying and attaching a patch to a biological tissue. The method comprising steps selected inter alia from:
a. obtaining a deployment and attachment device (DAD) comprising:
  i. deployment mechanism adapted to laterally deploy a patch; and,
  ii. at least one glue dispensing system (GDS), in communication with said deploying mechanism and said patch, adapted to attach said patch to a biological tissue within a body cavity via a biological glue 119;
said DAD is characterize by having a distal portion, adapted to be inserted into a body and a proximal portion, located adjacent to a user; said distal portion and said proximal portion are interconnected along a main longitudinal axis via a tube (103);
said tube (103) having a proximal end (TP) connected to said proximal portion, and a distal end (TD);
said tube (103) is adapted to at least partially accommodate a central shaft (105);
said central shaft (105) is characterized by a proximal end (CSP) accommodated within said tube and a distal end (CSD) protruding out of said TD; said central shaft is adapted to reciprocally move parallel to said main longitudinal axis within said tube;
said GR (116) is in communication with at least one glue dispensing tube (117);
said distal portion comprises:
  (i) at least two frame arms (FA) (104) adapted to be reversibly coupled to said patch;
  (ii) at least two proximal deployment arms (pDA) (108*a*, 108*b*) hinge-like connected to said TD and to the proximal end of said two FA;
  (iii) at least two distal deployment arms (dDA) (108*c*, 108*d*) hinge-like connected to said CSD and to the distal end of said two FA;
  each of said pDAs and dDAs (108*a*, 108*b*, 108*c*, 108*d*) is characterized by a plurality of configurations, at least one of said configurations is a parallel configuration in which each of said pDAs and dDAs is substantially parallel to said central shaft (105); and, at least one of said configurations is a substantially perpendicular configuration in which each of said pDA and dDA is substantially perpendicular to said central shaft (105);
  said FAs (104) are characterized by a closed configuration in which said pDAs and dDAs are in said parallel configuration; and, a deployed configuration at which said pDAs and dDAs are in said substantially perpendicular configuration such that said patch is deployed;
b. reversibly attaching said patch to said FAs;
c. adjusting said patch on said FAs;

d. introducing said distal portion into said body cavity;
e. reversibly transforming said FA from said closed configuration to said deployed configuration; thereby deploying said patch;
f. homogeneously dispersing glue 119 along substantially the entire margins area of said patch;
g. adjacently bringing said patch into contact with said biological tissue, thereby attaching said patch to said biological tissue.

It is another object of the present invention to provide the method as defined above, additionally comprising step of detaching said patch from said FA.

It is another object of the present invention to provide the method as defined above, additionally comprising step of transforming said FA from said deployed configuration to said closed configuration.

It is another object of the present invention to provide the method as defined above, additionally comprising step of extracting said DAD from said body cavity.

It is another object of the present invention to provide the method as defined above, additionally comprising step of laterally articulating said DAD so as said patch is orientated with respect to the treated defect.

It is another object of the present invention to provide the method as defined above, additionally comprising step of vertically articulating said DAD.

It is another object of the present invention to provide the method as defined above, additionally comprising step of reversibly coupling said GR 116 to said tube 103 prior to said patch insertion.

It is another object of the present invention to provide the method as defined above, additionally comprising step of selecting said glue from a group consisting of fibrin glue, Cyanoacrylate or any other glue suitable for clinical use.

It is another object of the present invention to provide the method as defined above, additionally comprising step of coupling said glue dispensing tube (117) to at least one selected from a group consisting of FA (104), pDA or dDA or any combination thereof.

It is another object of the present invention to provide the method as defined above, additionally comprising step of reversibly coupling said glue dispensing tube (117) to said patch (106).

It is another object of the present invention to provide the method as defined above, additionally comprising step of providing said GDT 117 with at least one nozzle 118 adapted to disperse said glue on said patch.

It is another object of the present invention to provide the method as defined above, additionally comprising step of inserting said nozzles 118 through said patch such that at least a portion of said nozzles 118 protrude out of said patch 106 prior to step (d) of introducing.

It is another object of the present invention to provide the method as defined above, additionally comprising step of selecting said patch to be a non-pores patch.

It is another object of the present invention to provide the method as defined above, additionally comprising step of internally coupling to said GR (116) at least one piston 302 adapted to reciprocal move along the GR's longitudinal axis such that said glue is extracted from said GR 116 to said GDT 117.

It is another object of the present invention to provide the method as defined above, additionally comprising step of driving said piston 302 by means selected from a group consisting of pneumatic means via compressed gas, mechanic means, hydraulic means or any combination thereof.

It is another object of the present invention to provide the method as defined above, additionally comprising step of accommodating within said GR 116 a multi-component glue.

It is still an object of the present invention to provide the method as defined above, additionally comprising step of dividing said GR 116 into at least two sealed sub cavities 308, 309 by at least one partition 310.

It is lastly an object of the present invention to provide the method as defined above, additionally comprising step of selecting the cross section area of said GDT 117 from an oval cross section so as to reduce the overall cross section area of said distal portion 101 in said 'closed configuration'.

BRIEF DESCRIPTION OF THE DRAWINGS

The invention is herein described, by way of example only, with reference to the accompanying drawings, wherein:

FIGS. 2A-2B illustrate the glue dispensing system (GDS);

FIGS. 3F-3G illustrate an alternative embodiment of said nozzle 118;

FIGS. 4F-4G illustrate another embodiment of the GR 116 in which a multi-component glue is utilized.

FIGS. 5C-5F illustrate the coupling process of the GR 116 to the tube 103 in a 3D isometric view and FIGS. 5G-5J respectively illustrate the same process in a lateral cross section.

DETAIL DESCRIPTION OF THE SPECIFIC EMBODIMENTS

Figure 1A:
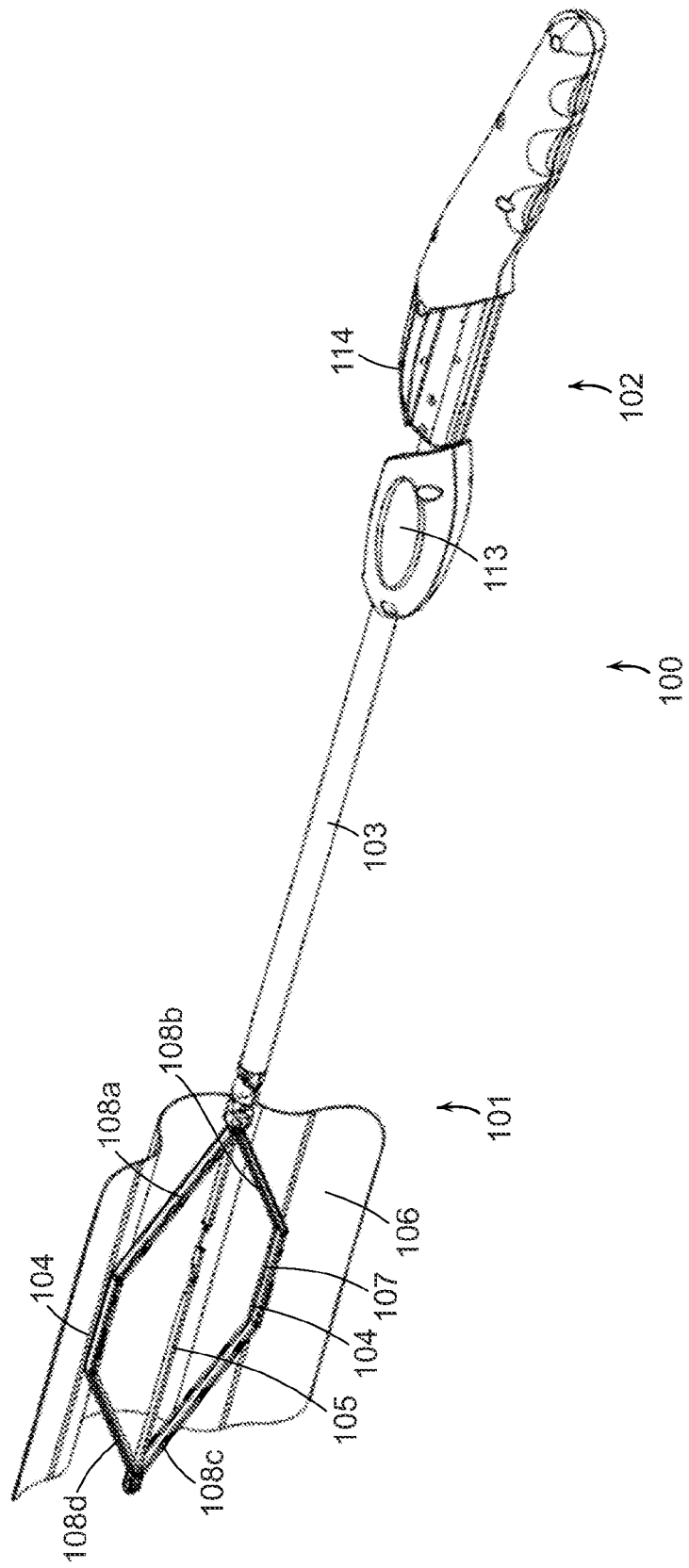
FIG. 1A illustrates an embodiment said PDD 100.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides means and method for providing a an attachment between a patch and a tissue via a biological glue.

The present invention provides a deployment and attachment device (DAD) which serves as a tool for insertion, deployment, placement and attachment of a prosthetic hernia mesh during laparoscopic hernia rapier surgery; wherein said DAD comprised a glue dispensing system (GDS) adapted to provide an attachment between said patch and the patient's tissue.

The present invention provides a deployment and attachment device (DAD) comprising:

c. deployment mechanism adapted to laterally deploy a patch; and, d. at least one glue dispensing system (GDS), in communication with said deploying mechanism and said patch, adapted to attach said patch to a biological tissue within a body cavity via a biological glue 119;

wherein said GDS comprising:

i. at least one glue reservoir (GR) 116 adapted to accommodate glue 119; and, ii. at least one glue dispensing tube (GDT) 117, in communication with said GR 116, adapted to homogeneously disperse glue 119 along substantially the entire margins area of said patch.

It is another object of the present invention to provide the DAD as defined above, wherein said DAD is characterize by having a distal portion, adapted to be inserted into a body and a proximal portion, located adjacent to a user; said distal portion and said proximal portion are interconnected along a main longitudinal axis via a tube (103);

said tube (103) having a proximal end (TP) connected to said proximal portion, and a distal end (TD);

said tube (103) is adapted to at least partially accommodate a central shaft (105);

said central shaft (105) is characterized by a proximal end (CSP) accommodated within said tube and a distal end (CSD) protruding out of said TD; said central shaft is adapted to reciprocally move parallel to said main longitudinal axis within said tube;

said GR (116) is in communication with said at least one glue dispensing tube (117);

said distal portion comprises:

(i) at least two frame arms (FA) (104) adapted to be reversibly coupled to said patch;

(ii) at least two proximal deployment arms (pDA) (108a, 108b) hinge-like connected to said TD and to the proximal end of said two FA;

(iii) at least two distal deployment arms (dDA) (108c, 108d) hinge-like connected to said CSD and to the distal end of said two FA;

each of said pDA and dDA (108a, 108b, 108c, 108d) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105);

said FAs (104) are characterized by a closed configuration in which said pDAs and dDAs are in said parallel configuration; and, a deployed configuration at which said pDAs and dDAs are in said substantially perpendicular configuration such that said patch is deployed; said FA are adapted to reversibly transform from said closed configuration to said deployed configuration by (i) said reciprocal movement of said central shaft (105) towards and away from said proximal portion; and, (ii) said transformation of each of said DAs from said parallel configuration to said perpendicular configuration, such that said deployment of said patch is at least partially reversible.

The present invention also provides a method for attaching a patch to a biological tissue during a surgery utilizing said DAD and GDS.

The method comprising steps selected inter alia from:

a. obtaining a deployment and attachment device (DAD) comprising:

i. deployment mechanism adapted to laterally deploy a patch; and, ii. at least one glue dispensing system (GDS), in communication with said deploying mechanism and said patch, adapted to attach said patch to a biological tissue within a body cavity via a biological glue 119; said GDS comprising: (a) at least one glue reservoir (GR) 116 accommodating glue 119; and, (b) at least one glue dispensing tube (GDT) 117, in communication with said GR 116;

b. attaching said patch to said DAD;

c. introducing said patch into said body cavity;

d. deploying said patch;

e. homogeneously dispersing glue 119 along substantially the entire margins area of said patch; and, f. adjacently bringing said patch into contact with said biological tissue, thereby attaching said patch to said biological tissue.

It is another object of the present invention to provide a method for deploying and attaching a patch to a biological tissue. The method comprising steps selected inter alia from:

a. obtaining a deployment and attachment device (DAD) comprising:

i. deployment mechanism adapted to laterally deploy a patch; and, ii. at least one glue dispensing system (GDS), in communication with said deploying mechanism and said patch, adapted to attach said patch to a biological tissue within a body cavity via a biological glue 119;

said DAD is characterize by having a distal portion, adapted to be inserted into a body and a proximal portion, located adjacent to a user; said distal portion and said proximal portion are interconnected along a main longitudinal axis via a tube (103);

said tube (103) having a proximal end (TP) connected to said proximal portion, and a distal end (TD);

said tube (103) is adapted to at least partially accommodate a central shaft (105);

said central shaft (105) is characterized by a proximal end (CSP) accommodated within said tube and a distal end (CSD) protruding out of said TD; said central shaft is adapted to reciprocally move parallel to said main longitudinal axis within said tube;

said GR (116) is in communication with at least one glue dispensing tube (117);

said distal portion comprises:

(i) at least two frame arms (FA) (104) adapted to be reversibly coupled to said patch;

(ii) at least two proximal deployment arms (pDA) (108a, 108b) hinge-like connected to said TD and to the proximal end of said two FA;

(iii) at least two distal deployment arms (dDA) (108c, 108d) hinge-like connected to said CSD and to the distal end of said two FA;

each of said pDAs and dDAs (108a, 108b, 108c, 108d) is characterized by a plurality of configurations, at least one of said configurations is a parallel configuration in which each of said pDAs and dDAs is substantially parallel to said central shaft (105); and, at least one of said configurations is a substantially perpendicular configuration in which each of said pDA and dDA is substantially perpendicular to said central shaft (105);

said FAs (104) are characterized by a closed configuration in which said pDAs and dDAs are in said parallel configuration; and, a deployed configuration at which said pDAs and dDAs are in said substantially perpendicular configuration such that said patch is deployed;

b. reversibly attaching said patch to said FAs;
c. adjusting said patch on said FAs;
d. introducing said distal portion into said body cavity;
e. reversibly transforming said FA from said closed configuration to said deployed configuration; thereby deploying said patch;
f. homogeneously dispersing glue 119 along substantially the entire margins area of said patch;
g. adjacently bringing said patch into contact with said biological tissue, thereby attaching said patch to said biological tissue.

It should be emphasized that some of the major advantages of the present invention, with respect to the prior art, is to provide a fast and reliable method for dispensing glue on top of a hernia mesh/patch during laparoscopic hernia surgery, thus, enabling an attachment between the patch and the patient's tissue.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components.

The term "hinge like connection" can refer to a standard hinge or to a living hinge (i.e., a thin flexible hinge (flexure bearing) made from plastic that joins two rigid parts together while allowing them to bend along the line of the hinge).

The term "biological glue" refers hereinafter to any biological glue which can provide adhesion between a living biological tissue and a synthetic or biological material (e.g., hernia patch/mesh); thus, providing an attachment between said tissue and said patch/mesh. The glue can be either multi component glue—e.g. fibrin glue or fibrin sealant (FS). Or single component glue—e.g. Cyanoacrylate or any other glue suitable for clinical use.

The term 'controlled deployment' refers hereinafter to a patch deployment which is continuous; i.e., the deployment is not binary but analogous—there are several deployment levels. This is in contrast so conventional deployment system is now days (see for example U.S. Pat. No. 5,370,650), in which the deployment of the patch relies upon the elasticity of a loop member surrounding the patch such that the patch can be either fully folded or fully unfolded. No intermediate are enabled. In the present invention there can be several deployment stages.

According to a preferred embodiment of the present invention, the DAD device provided is adapted to provide a controlled deployment of the patch.

The term 'bidirectional' or 'fully reversible deployment' refers hereinafter to the deployment of the patch, which according to the present invention, is fully reversible. In other words, the patch deployment is bidirectional, i.e., the patch can be fully folded (i.e., deployed within the body) and then, if the surgeon desires, the patch can be fully unfolded simply by the reconfiguration of the flexible arms from the initial stage to the final stage and vice versa.

According to a preferred embodiment of the present invention, the DAD device provided is adapted to provide a bidirectional or fully reversible deployment of the patch.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh within the abdominal cavity so as to fit to the hernia. Usually the mesh is not symmetric in shape (i.e., rectangular or i.e., ellipse)—therefore it has different directions. By rotating the mesh within the abdominal cavity—one can decide which direction is turned where.

The term "adjusting" refers hereinafter to rolling, folding and winding of the patch, thus preparing and enabling the insertion of said patch into the abdominal cavity.

The term "lateral deployment" refers hereinafter to a deployment in which the plane of the deployed patch is substantially parallel to the main longitudinal axis of the trocar or the DAD 100 and hence of the tube 103 or the central shaft 105.

Figure 6:
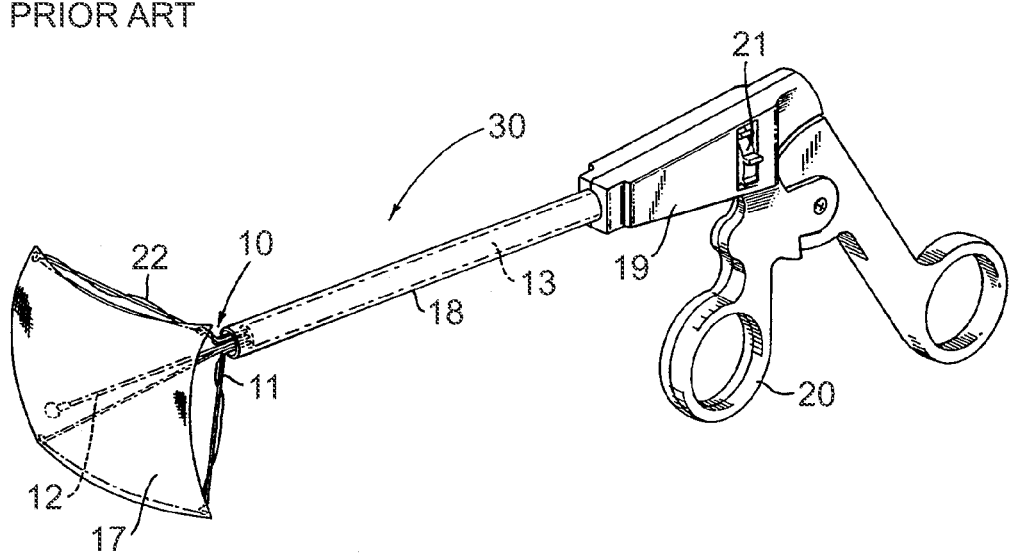
FIG. 6 illustrates a perpendicular deployment.

The term "perpendicular deployment" refers hereinafter to a deployment in which the plane of the deployed patch is substantially is perpendicular to the main longitudinal axis of the DAD 100 or the trocar). An example of a perpendicular deployment is given in FIG. 6, which is a preferred embodiment of the deployment illustrated in U.S. Pat. No. 5,405,360.

Before explaining the figures, it should be understood that the invention is not limited in its application to the details of construction and the arrangement of the components set forth in the following description or illustrated in the drawings. The invention can be carried out in various ways.

Generally speaking, each deployment and attachment device (DAD) 100 comprises at least two portions: a distal portion 101 and a proximal portion 102. The proximal portion is adapted to remain outside the body, adjacently to the user and the distal portion 101 is adapted to be inserted into the body.

The distal portion comprises at least one frame arm 104 to which the patch is attached to. The distal portion is characterized by two main configurations: a 'closed configuration' in which the DAD enables insertion of said mesh into the abdominal cavity and 'deployed configuration' in which the patch 106 is spread via the distal portion outer frames.

Reference is now made to FIG. 1A illustrating an embodiment said DAD 100. As described, the DAD 100 comprises (i) a deployment mechanism adapted to deploy and to enable proper placement of the patch within the abdominal cavity; and, (ii) an attachment mechanism between the patch and the biological tissue.

The attachment mechanism disclosed in the present application is a glue dispensing system (GDS) which attaches said patch to a biological tissue within a body cavity via a biological glue.

The DAD comprises two main portions: distal portion 101, and a proximal portion 102. The two portions are interconnected via a tube 103.

The distal portion 101 is adapted to be reversibly inserted into a body cavity (namely the abdominal cavity) during a surgery (namely, minimal invasive surgeries) via a trocar.

The distal portion enables the deployment and the properly orientation and placement of a prosthetic hernia repair patch 106 with respect to the patient's tissue 120 surface.

The distal portion comprises:
(a) at least two frame arms (FA) 104;
(b) at least 4 deployment arms (DA) 108; and, (c) a central shaft 105 (which interconnects the distal portion and the proximal portion of to DAD 100) adapted to reciprocally move within tube 103.

It should be emphasized that the main role of the central shaft is to provide the DAD in the deployed configuration with sufficiently stiffness and back support (to the deployed patch) so as to provide a rigid enough device that allows proper mesh rolling and insertion, especially when dealing with large and thick patches.

The DAs 108 can be divided into two groups: 2 DAs (108*a* and 108*b*) which are proximally located with respect to tube 103 and 2 DAs (108*d* and 108*c*) which are distally located with respect to tube 103.

The proximal DAs (108*a* and 108*b*) are connected to the tube's 103 distal end and to the FA 104. The distal DAs (108*c* and 108*d*) are connected to the central shaft 105 and to the FAs 104. All said connections are hinge connections.

Each of said DAs (108) is characterized by a plurality of configurations. One of said configuration is a parallel configuration in which the DA is substantially parallel to said central shaft (105).

Another one of said configuration is an angled configuration in which said DA are located at an angle A with respect to said central shaft (105). Angle A can be at a range of about 0 degrees to about 180 degrees.

In the 'closed configuration' the deployment arms (DA) 108 are in the parallel configuration and in the 'deployed configuration' the deployment arms (DA) 108 are in the substantially perpendicular configuration (i.e., Angle A is about 90 degrees).

Figure 1B:
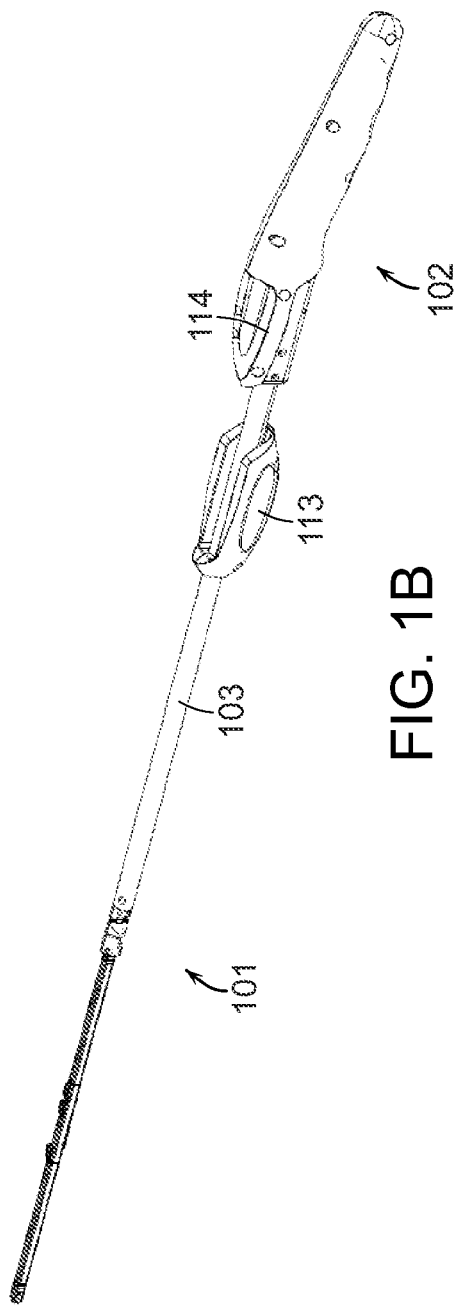
FIG. 1B illustrates the close configuration of said PDD 100.
Figure 1C:
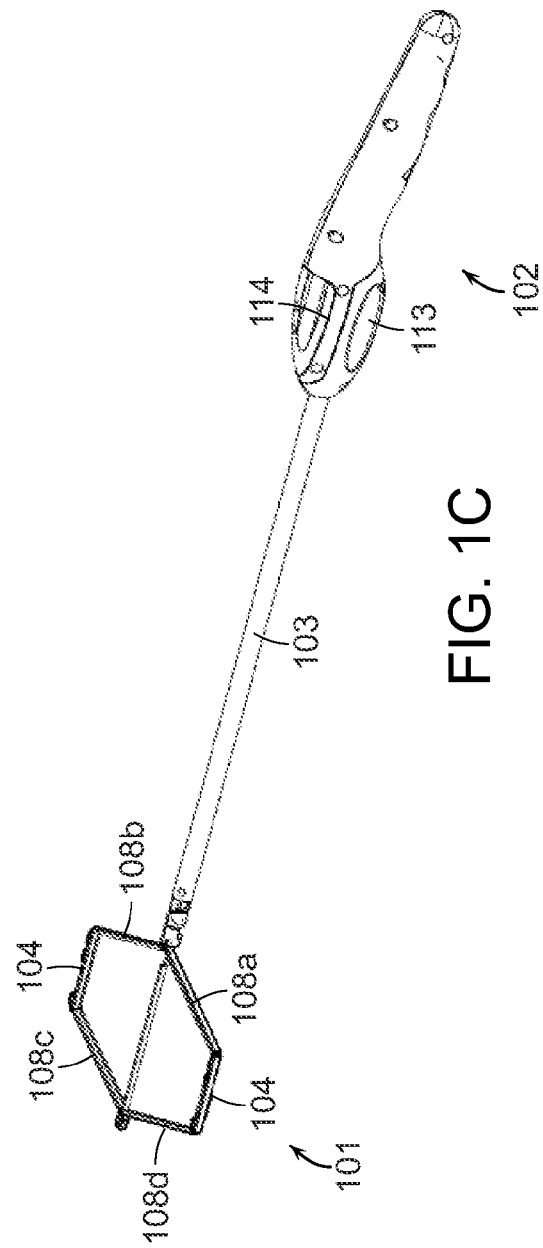
FIG. 1C illustrates the deployed configuration of said PDD 100.

Reference is now made to FIGS. 1B-1C which illustrate the DAD 100 in its close configuration and in its deployed configuration. The close configuration is described in FIG. 1B while the deployed configuration is describe in FIG. 1C.

In the parallel configuration of said DAs 108 the DAD 100 is in its close configuration and in the angled configuration of said DAs 108, the DAD 100 is in its deployed configuration.

It should be emphasized that the patch deployment mechanism disclosed in the present application enables a patch deployment which is lateral deployment (i.e., the patch is deployed substantially parallel to the main longitudinal axis of the DAD 100 and hence of the tube 103 or the central shaft 105).

Such a deployment has several advantages over a perpendicular patch deployment mechanism (i.e., the plane of the deployed patch is perpendicular to the main longitudinal axis of the device or the trocar), among which the following:

(1) Since in most cases the patch is inserted laterally with respect to the hernia defect, a perpendicular deployment will require a great amount of articulation in order to bring the patch into proper alignment with respect to the hernia defect. Such amount of articulation performance will be extreme difficult to perform at the confined abdominal space;

(2) The fact that the patch is deployed substantially perpendicularly to the trocar limits the size of the patch that can be used. In a perpendicular deployment (as in lateral deployment), the entire patch's size has to be introduced into the abdominal cavity, since the abdominal cavity has no sufficient depth to allow such spreading/deployment of large patches (i.e. larger than about 15 cm at one of their edges), the size of the patches that could be used will be limited.

The patch/mesh/net 106 is reversibly attached to the FAs 104 by at least one reversible connection clip (CC) 107, adapted to hold said patch 106 attached to DAD 100 during adjustment of the patch (e.g., rolling and insertion into the abdominal cavity) and during the deployment of said patch.

Since the CCs 107 enable a reversible attachment between the patch and the DAD, the CCs 107 additionally allow detachment between said patch 106 and the DAD 100 once the patch 106 is substantially secured to the tissue 120.

Said CCs 107 can be an integral part of the FAs 104 or a separate part which are combined and secured to the DAD 100 during the product assembly.

According to one embodiment, the distal portion 101 can be rotated laterally (i.e. left and right with regards to tube 103) and vertically (i.e. up and down with respect to the tube 103), such that the patch could be properly aligned and oriented within the abdominal cavity with regards to the hernia. Said lateral articulation is controlled by at least one articulation wire 110.

The proximal portion 102 comprises a deployment lever 113 which provides the surgeon with the ability to control the deployment process; and an articulation lever 114 which provides the surgeon with the ability to control lateral articulation angle of the distal portion.

Figure 1D:
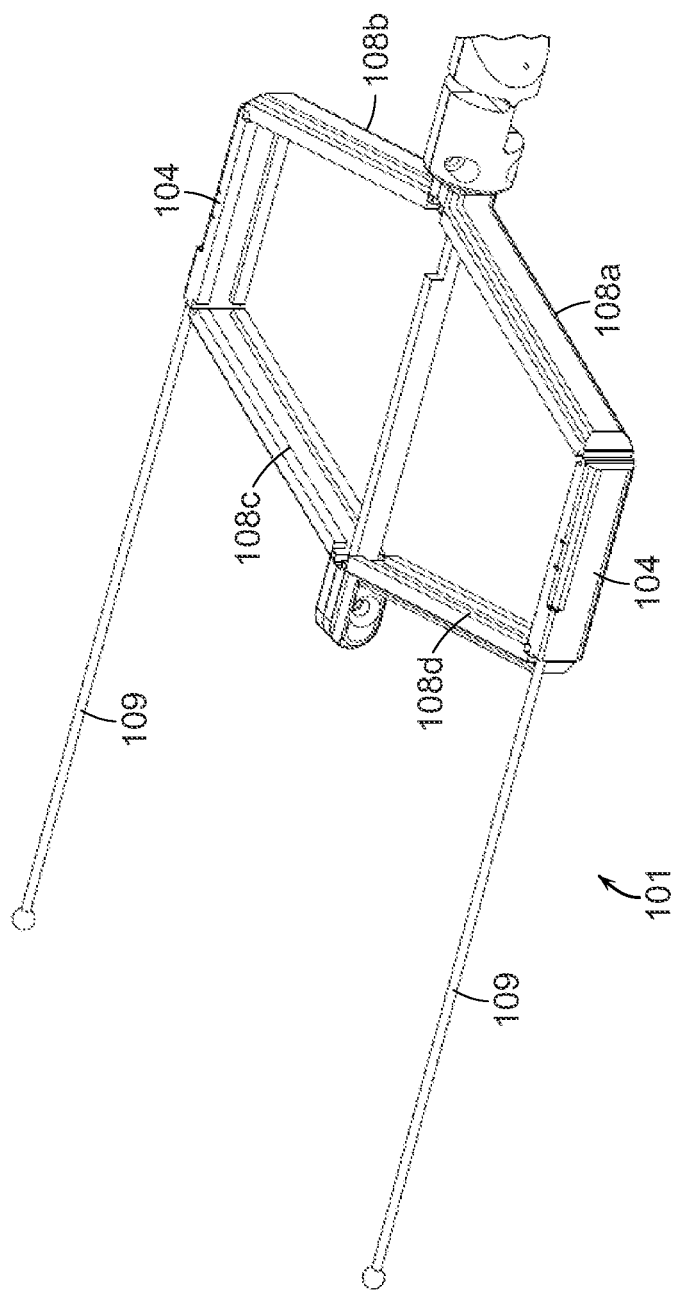
FIG. 1D provides a closer view of the distal portion of the DAD 100 in the deployed configuration.

Reference is now made to FIG. 1D which provides a closer view of the distal portion of the DAD 100 in the deployed configuration.

The figure also illustrates another embodiment of the present invention, in which extension arms 109 are provided. Such arms 109 are merely extensions of FAs 104 and are adapted to provide better support for patch 106.

Figure 2B:
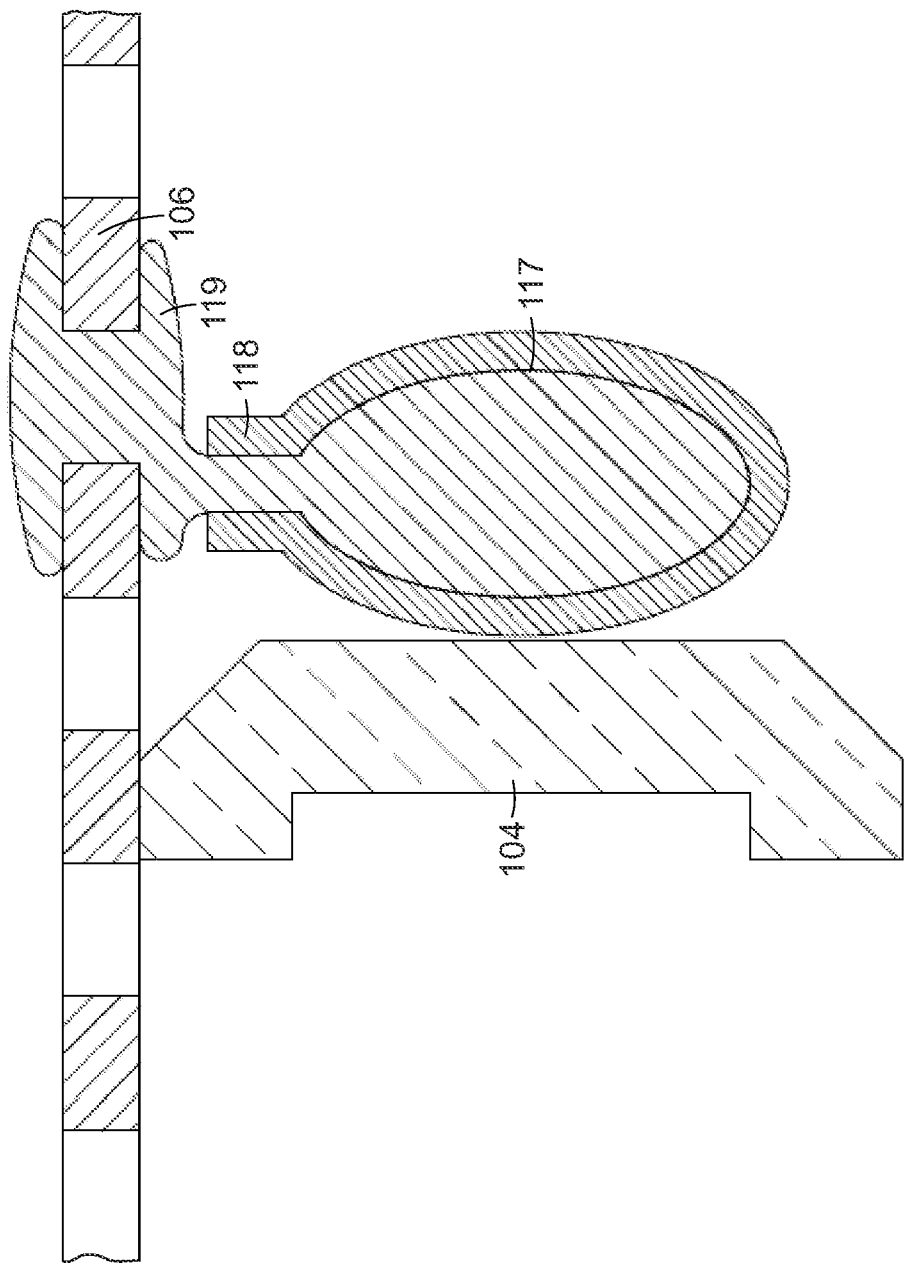

Reference is now made to FIGS. 2A and 2B illustrating the glue dispensing system (GDS). In general, the glue dispensing system (GDS) 115, as provided by the present invention, comprises a glue reservoir (GR) 116, which contains glue 119, and at least one glue dispensing tube (GDT) 117.

Each GDT 117 comprises at least one nozzle 118 from which glue 117 exits.

Once the patch 106 is deployed within the patient's abdominal cavity (but before it comes into contact with the tissue) said glue 119 is forced out from the glue reservoir (GR) 116 via said GDT 117 and said nozzle 118.

According to one embodiment of the present invention, the glue is homogeneously spread on the patch prior to any contact between the patch and the tissue. Said glue is spread on the tissue prior to any contact so as to enable said glue to better disperses on the patch and to provide homogeneously spreading.

It should be emphasized that each DAD 100 can comprise one or more GDS 115.

Once the glue comes out of nozzle 118, it is spread on top of the patch 106. Once the glue 119 covers at least a portion of the top surface of the patch 106, the surgeon can place the patch at its desired location on the patient's tissue, via said DAD 100.

According to a preferred embodiment of the present invention, the glue is spread near the perimeter of the patch.

Once suitable adhesion between patch 106 and the tissue 120 is obtained, DAD 100 is disconnected from the patch 106, along with said GDS 115, and extracted out of the patient's body.

The present invention discloses several embodiments of said GDS 115.

Reference is made again to FIGS. 2A1, 2A2-2B which describe one embodiment of said GDS 115. According to this embodiment said glue reservoir (GR) 116 is located as close as possible to the distal end of the DAD 100.

Placing the GR 116 as close as possible to the distal end of the DAD minimized the total length of the GDT 117 needed, such that the path length in which the glue 'travels' prior to reaching the patch is minimized. Therefore, the amount of wasted glue is minimized.

According to this embodiment, the GDT 117 encircles the distal end of said DAD 100 (i.e., the frame arms FA 104 and the deployment arms 108) and forms a loop around the same such that, when the patch is deployed, the GDT is in contact with substantially the entire perimeter (i.e., the outer surface or margins) of said patch so as to dispense the glue on said perimeter (i.e., outer surface or margins) of the patch. In such a way the contact area is increased and hence a better attachment is provided.

Such a feature is highly important since it provides better/stronger attachment between the tissue and the patch. Said better attachment is enabled since the glue is dispersed over a surface (preferably over the entire the outer surface or margins) of the patch which provides a plurality of contacts points.

This is in contrast to an attachment mechanism which provides attachment in a few preselected contact points; such an attachment is likely to provide a weak attachment.

The two ends (117a, 117b, see FIG. 2A2) of the loop formed from said GDT 117 are connected to the GR 116 such that glue can be extracted from the two end of said GDT 117 so as to better optimize the glue dispersing onto the patch.

GDT 117 is attached to the frame arms FA 104 and the deployment arms 108 of the DAD 100 such that once the distal portion 101 is in its 'deployed configuration', said GDT 117 is located substantially along the edges of said patch 106.

Reference is now made to FIG. 2A2 which illustrates the distal portion of the DAD in which the GDT 117 is coupled to the FA 104 and the deployment arms 108 and is located substantially on the perimeter of the patch 106 (the patch 106 is not shown).

According to one embodiment, the GDT 117 is characterized by an oval cross section in order to reduce the overall cross section area of the distal portion 101 while it is in its 'closed configuration'.

According to another embodiment, the GDT 117 comprises numerous nozzles 118, each of which is facing the patch 106.

According to this embodiment patch 106 used is porous, therefore, once glue 119 flows out of nozzles 118 to the bottom side of patch 106 (i.e. the side facing the viscera) it passes through the pores of the patch 106 to its top side (i.e. the side facing the fascia), thus forming an adhesive layer along patch's 106 edges (see FIG. 2B).

Once the glue is applied, the surgeon can press patch 106 to the tissue 120 in its proper location with respect to the tissue 120.

Once the glue is substantially cured, the DAD 100, together with the GDS 116 can be detached from patch 106 and extracted out of the patient's body.

Figure 3A:
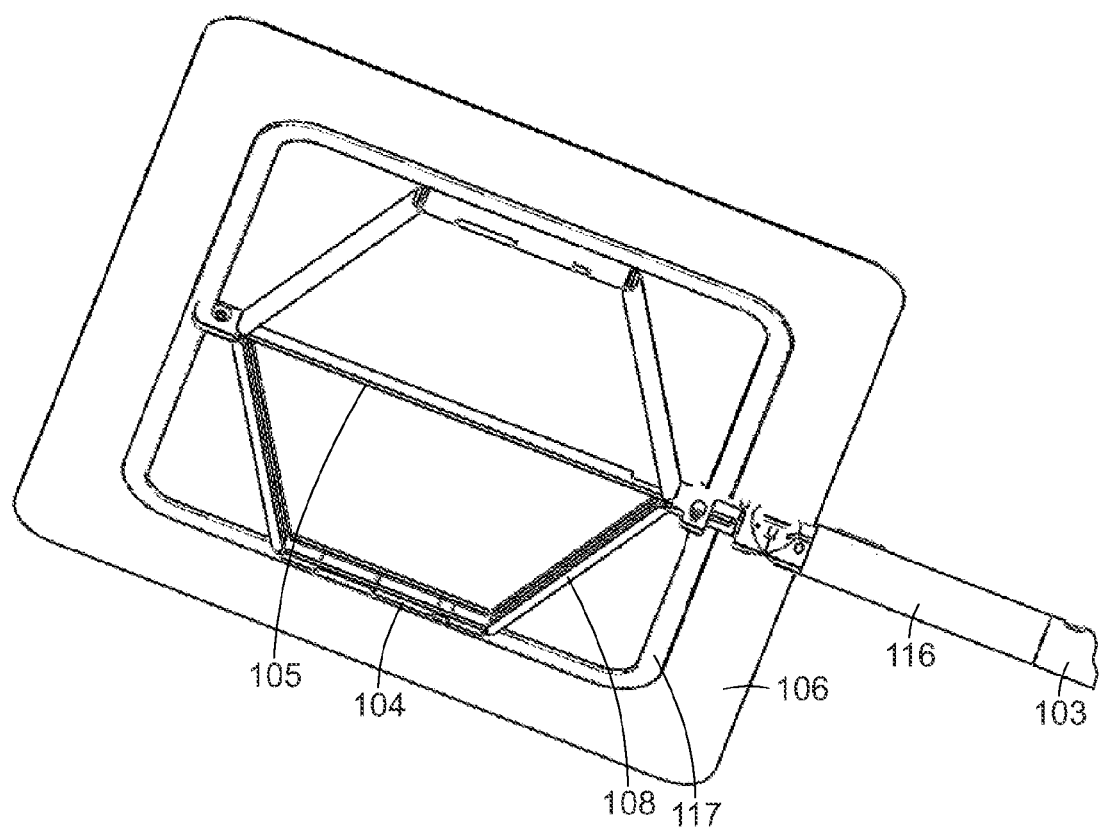
FIGS. 3A-3B illustrate another embodiment of PDD 100 and GDS 115 in which said glue 119 is applied directly to the top side of said patch 106.
Figure 3B:
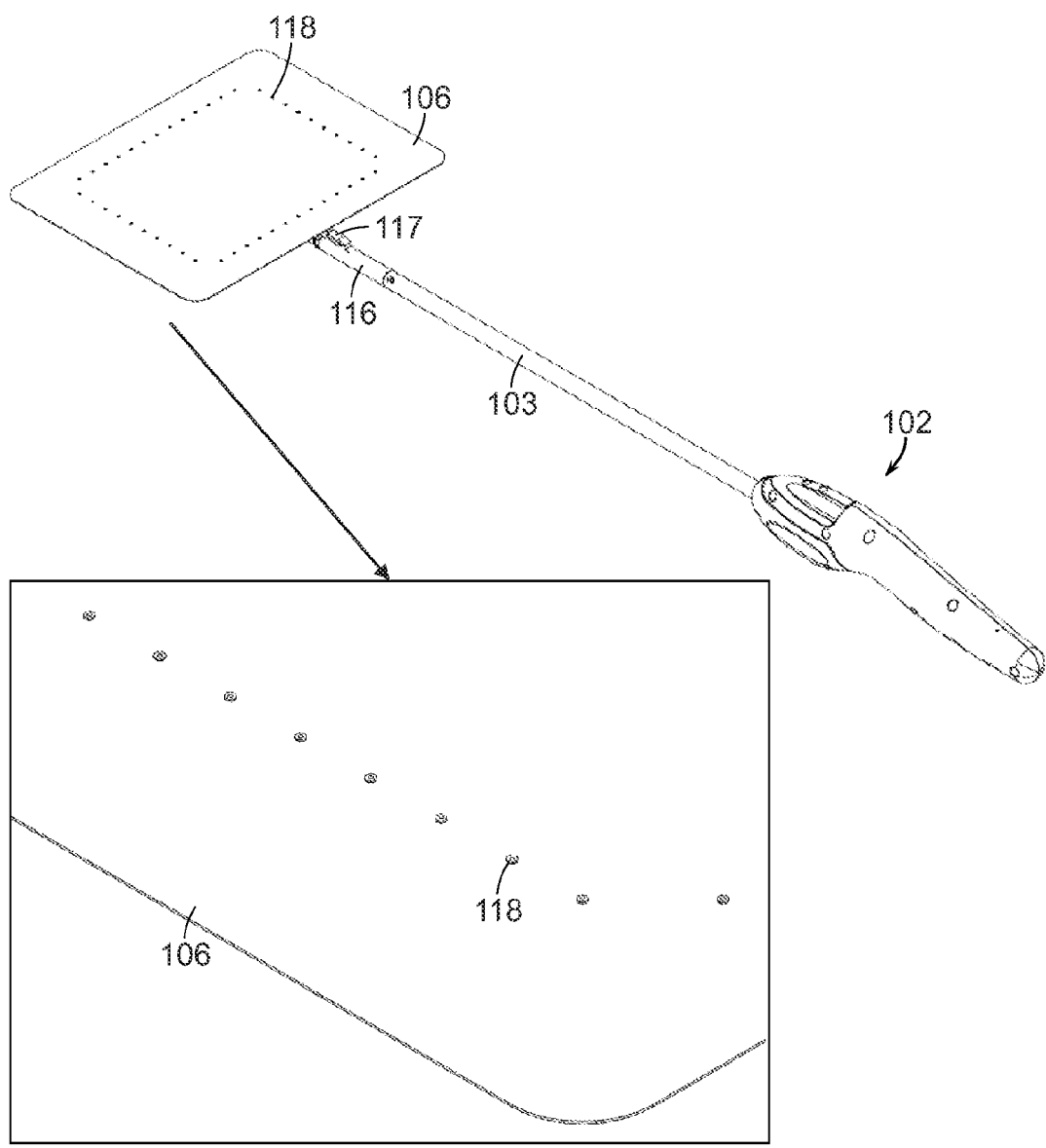
Figure 3C:
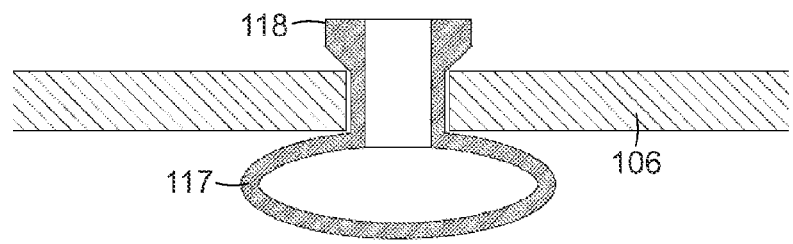
FIGS. 3C-3D which illustrate a cross section view of a single nozzle 118 and describes the gluing process.

Reference is now being made to FIGS. 3A-3C illustrating another embodiment of DAD 100 and GDS 115 in which said glue 119 is applied directly to the top side of said patch 106.

Such direct application is required when non porous patches are utilized; hence the glue can not pass through the patch.

According to this embodiment, the GDT 117 is pre-connected to patch 106 such that each of the nozzles 118 are pre inserted through said patch and emerge out of the top side of patch 106.

In such a way the top end of each of the nozzles 118 protrude out of the top section of the patch 106 (see FIGS. 3A, 3B and 3C).

In a preferred embodiment, an attachment between GDT 117 and patch 106 can be obtained via the special configurations of the nozzles 118 (e.g., an expanding top portion which 'holds' the GDT 117 to the patch 106).

The GDT 117 can be rolled and inserted together with patch 106 (see FIG. 3A) while the GDT 117 is attached to DAD 100 in at least one section, preferably only at the FAs 104.

Figure 3D:
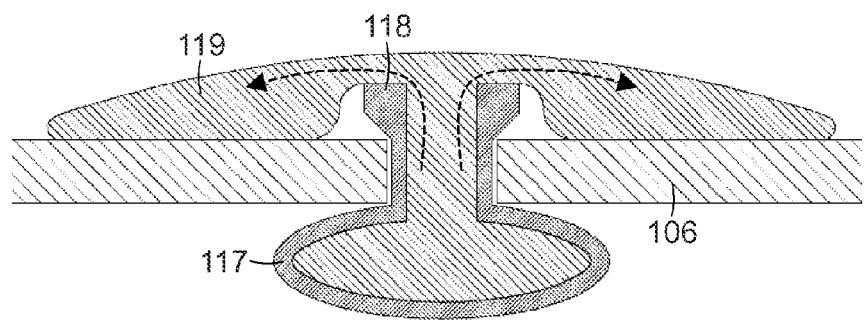

Reference is now being made to FIGS. 3C-3D which illustrate a cross section view of a single nozzle 118 during the gluing process.

According to this embodiment, at the initial stage, GDT 117 and nozzles 118 contains no glue (see FIG. 3C), such that GDT 117 can collapse to its minimal cross section while it is rolled together with the patch 106.

Once the patch is inserted to the abdominal cavity and deployed, glue 119 is forced out from GR 116 into GDT 117 and out of nozzle 118 on top of patch 106, forming an adhesive layer (see FIG. 3D).

Next, patch 106 is forced onto the tissue 120, via the DAD 100 (said step is needed in order to obtain said adhesion between patch 106 and tissue 120).

Figure 3E:
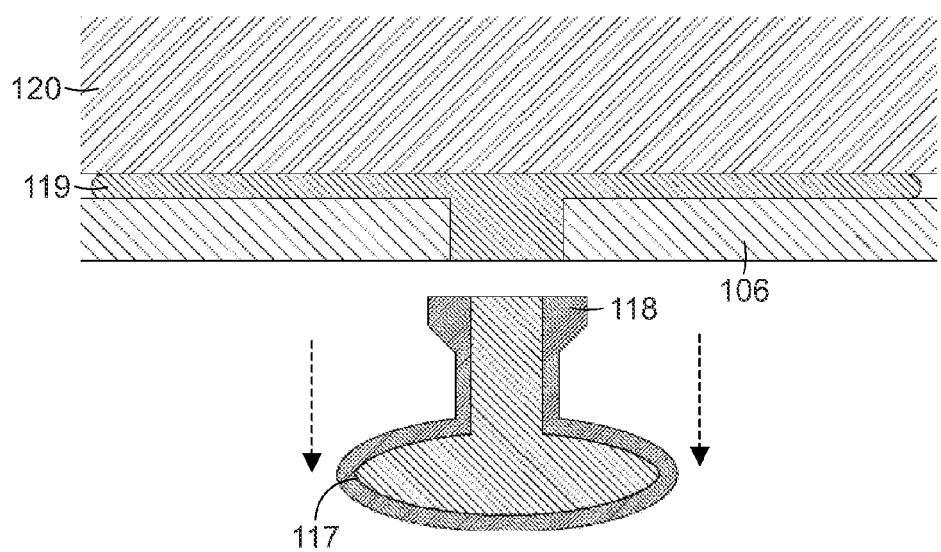
FIG. 3E illustrates the detachment between the distal portion 101 and the patch 106.

Once glue 119 is cured, the distal portion is pulled away from tissue 120. Said pulling detaches the distal portion 101 from the patch 106. Since the GDT 117 is connected to the distal portion (e.g., to the FAs 104 or to the DAs 108) it is also pulled away from the patch (see FIG. 3E).

Reference is now being made to FIGS. 3F-3G which describe an alternative embodiment of said nozzle 118.

According to one embodiment, described in FIG. 3F, nozzle 118 comprises at least two openings facing two opposite directions.

Such configuration increases the patch's area which comes into contact with the glue, once the glue 119 is forced out of the nozzle 118. Furthermore, such an embodiment can provide said attachment between the patch and the GDT 117.

According to another embodiment described in FIG. 3G, two nozzles 118 emerge out of GDT 117 in a tilted direction. The nozzles are inserted to patch in two separate points, therefore providing an improve glue dispensing coverage; in addition this configuration is preferable since this configuration also holds GDT 117 attached to patch 106.

Reference is now being made to FIGS. 4A-4E which describes an embodiment of the GR 116. According to this embodiment said GR 116 is characterized by an elongated cylinder coupled to the tube 103 at its distal end (see FIG. 4A).

Said cylinder comprises at least one hollow channel 301 along its longitudinal axis. Said channel 301 allows the central shaft 105 and the articulation wire 110 to pass through the GR 116 to the distal portion 101 of the DAD.

Figure 4A:
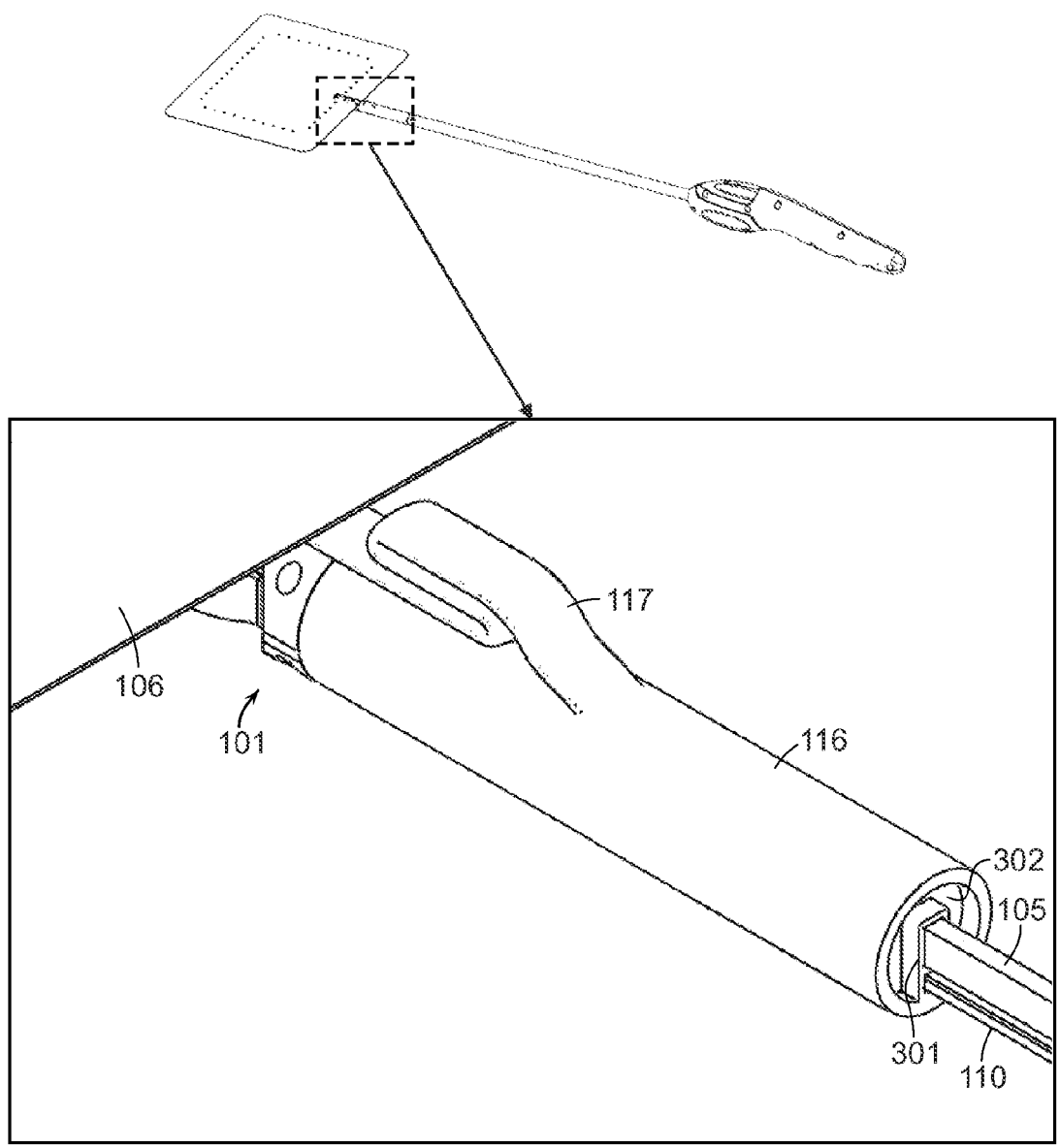
FIGS. 4A-4E illustrates another embodiment of the GR 116.

It should be mentioned that for the purpose of illustration only, tube 103 was removed from FIG. 4A.

A piston 302 is located inside the GR 116 and partially encircles the channel 301. The piston 302 is adapted to reciprocal move along the GR's longitudinal axis.

GDT 117 is connected to the distal portion of said GR 116.

Piston 302 is adapted to reciprocally move within the internal cavity of said GR 116 along the longitudinal axis of the same.

Figure 4B:
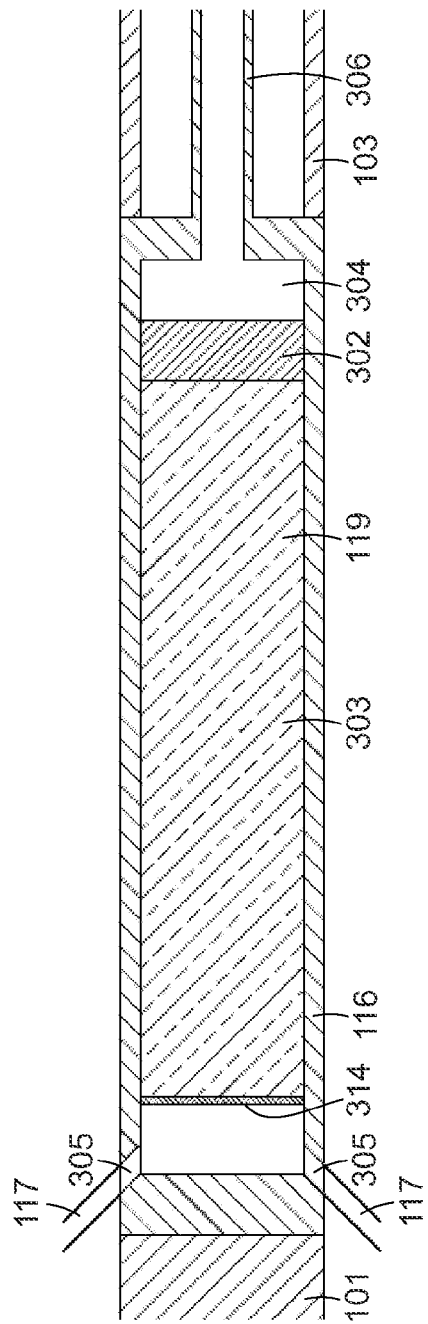

Said piston 302 divides the internal cavity of said GR 116 into two separate cavities: a glue cavity 303 and an empty back cavity 304 (see FIG. 4B).

Said glue 119 is initially located inside the glue cavity 303 which capture the entire GR 116 internal space (i.e., the empty back cavity 304 is close to nothing). As piston 302 moves towards the distal portion of the DAD the empty cavity 304 enlarges while the glue cavity decreases (since the glue is extracted from the GR 116 and into the GDT 117).

A membrane 314 is located at the distal end of the glue cavity 303, and prevents the glue from entering said GDT 117 before glue activation (i.e., the membrane 314 prevent the glue from exiting the GR 116 during e.g., storage and device insertion).

At least one aperture 305 is located at the distal end of the GR 116 through which said glue 119 is forced into the GDT 117. While the glue 119 is compressed by piston 302, membrane 314 bursts, allowing the glue to flow to GDT 117 through aperture 305.

Figure 4C:
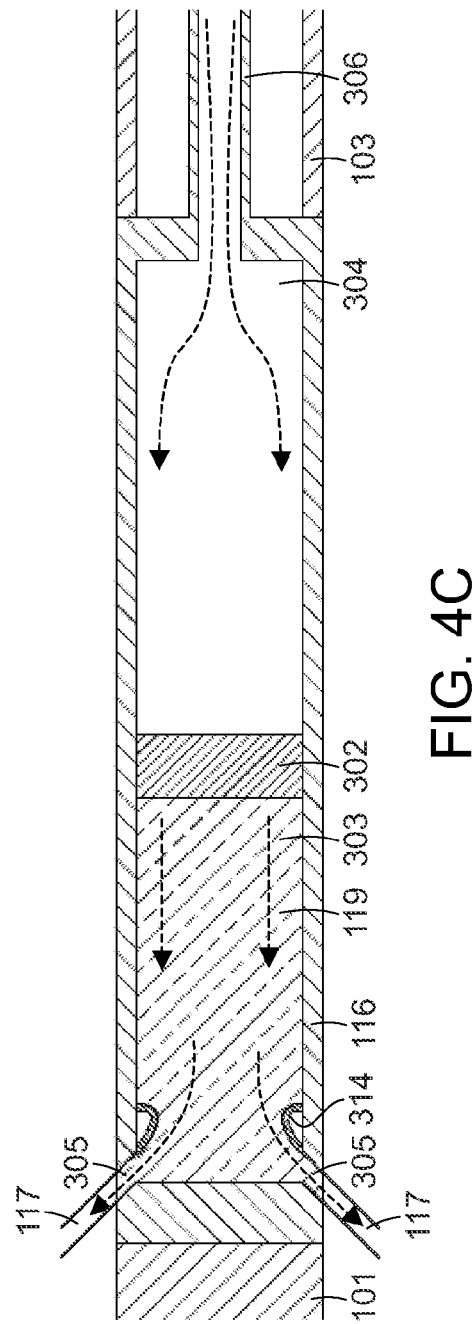
Figure 4D:
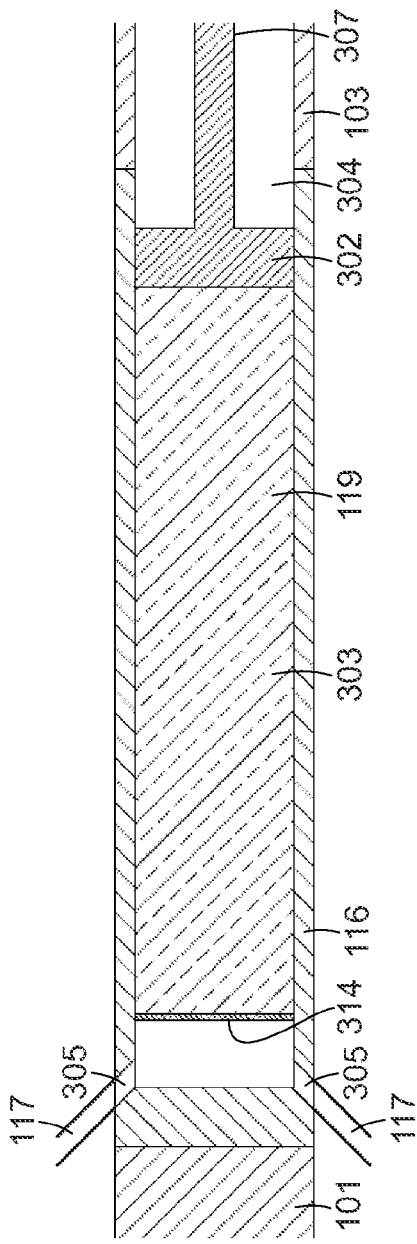
Figure 4E:
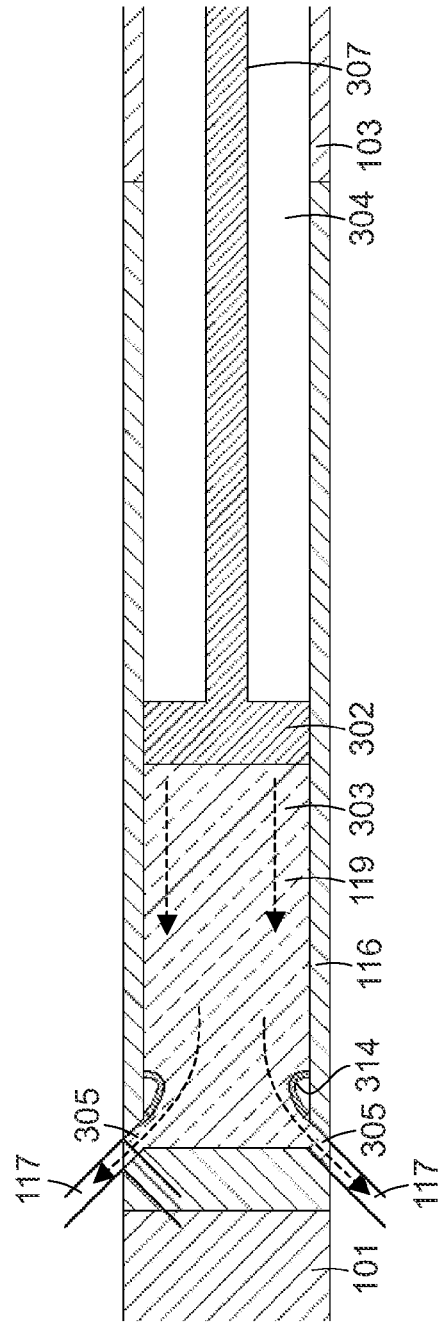

According to this embodiment, said forcing (i.e., application of force on the glue) is performed by pushing piston 302 toward the distal end of GR 116 (see FIG. 4C).

The piston can be pneumatically driven forward by filling the back cavity 304 with a compressed gas coming from a compressed gas canister located at the proximal portion 102.

The gas passes through tube 306. Alternatively, said piston 302 can be mechanically pushed forward by a shaft 307 coming from the proximal portion 102 (see FIGS. 4D-4E).

Reference is now being made to FIGS. 4F-4G which describes another embodiment of the GR 116 which utilizes multi-component glue (e.g. fibrin glue).

According to this embodiment, the internal cavity of said GR 116 is divided to several sub cavities 308, 309 by at least one partition 310. Each cavity 308, 309 is connected to a single mixing cavity 311 via holes 312, 313 located at the distal end of each cavity 308, 309. Said holes 312, 313 are initially blocked by two membranes 314 which prevents early mixing of the glue components during shipping and storage. Said membranes 314 is adapted to collapse once the two glue components are forced out by pistons 302. Said mixing cavity 311 is connected to the GDT 117 by at least one aperture 305 located at the distal portion of said GR 116. Once dispensing of the glue is required, piston 302 is pushed forward, either pneumatically, hydraulically or mechanically, hence forcing the glue components from the cavities 308, 309, into the mixing cavity 311. In the mixing cavity 311 the two glue components are mixed, and flow into the GDT 117 through aperture/s 305 (see FIG. 4G).

It should be pointed out that using two components glue (such as fibrin sealant), the GR 116 will accommodate the two compounds in two separate and sealed compartments, such that no mixing of the two components during storage occurs.

Reference is now being made to FIGS. 5A-5D which describe an embodiment of said GR 116. According to this embodiment the GR 116 is provided as a separate part from said DAD 100. Furthermore, said GR 116 can be assembled by the medical staff at the operation room prior to the insertion of the device into the abdominal cavity.

In such an embodiment, the glue can be stored separately and far away from the DAD 100. Such separate storing of the glue is needed when ever the glue 119 requires special storage condition (e.g., cryogenic cooling).

Providing a device which enables a reversible coupling between a glue reservoir and the DAD 100 is highly important and advantageous in cases which the glue require special storage condition (e.g. cryogenic cooling) prevent from the entire device being stored in a special storage facility, substantially increasing operation costs.

According to this embodiment, the GR 116 is cylindrically shaped and is characterized by a cross sectional area and diameter which are identical to the diameter of tube 103.

The GR 116, as was described above, is open at its proximal end. The GR 116 is characterized by a groove 501 along its bottom side (see FIG. 5A).

A hollow bar 502 (which is an integral part of the tube 103, see FIG. 5B) is adapted to be fitted within said groove 501.

Bar 502 is hollow so as to allow the central shaft 105 and the articulation wires 110 to pass through it to the distal portion 101.

Piston 302 is characterized by the same dimensions and shape as of the internal dimensions of cylinder. Yet more, piston 302 is adapted to reciprocally move along its longitude axis (see FIG. 5A). The movement of said piston applies pressure on the glue and presses the glue 119 out of GR 116 and into GDT 117.

Once GR 116 is coupled to tube 103, piston 302 can be pressed forward (towards the distal end of the DAD 100) by at least one rod 505 (see FIG. 5B); alternatively said pressing can be accomplished by hydraulic or pneumatic means.

Figure 5A:
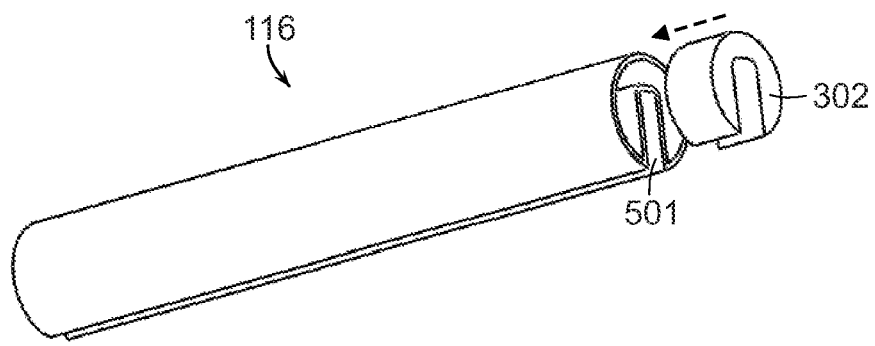
FIGS. 5A-5D which illustrate another embodiment of said GR 116.
Figure 5B:
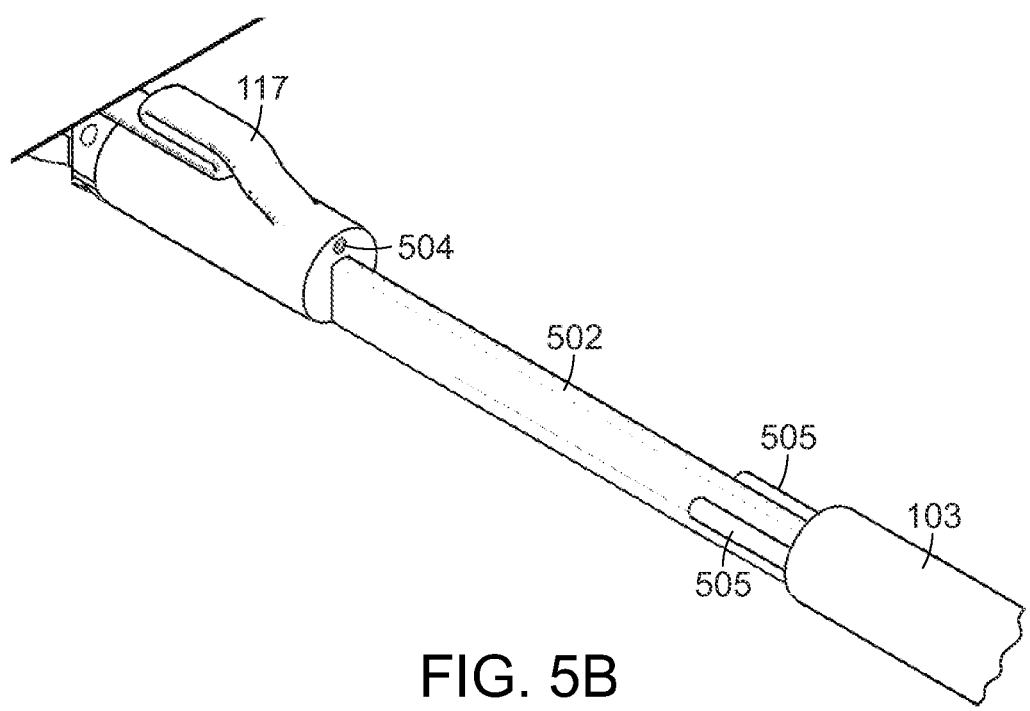
Figure 5C:
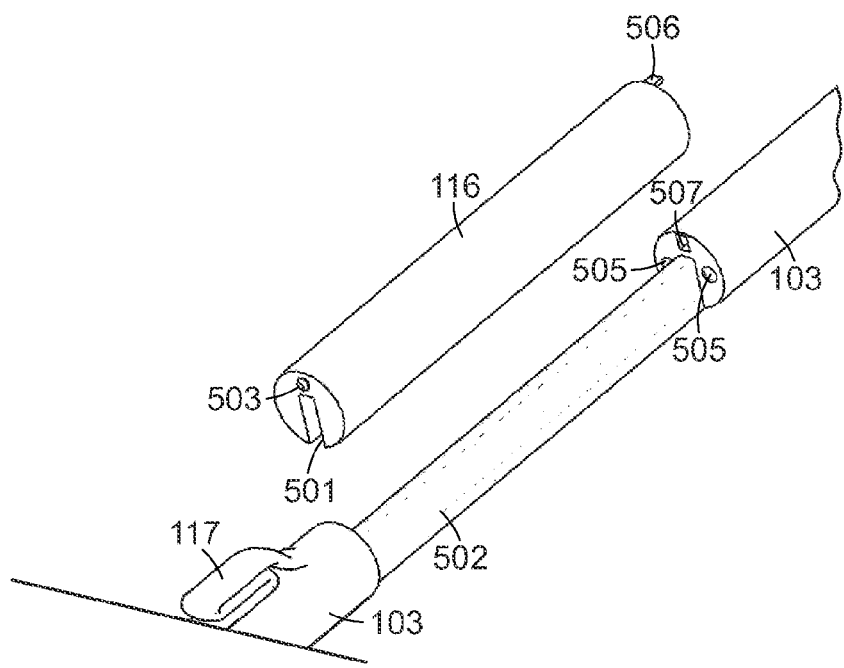
Figure 5D:
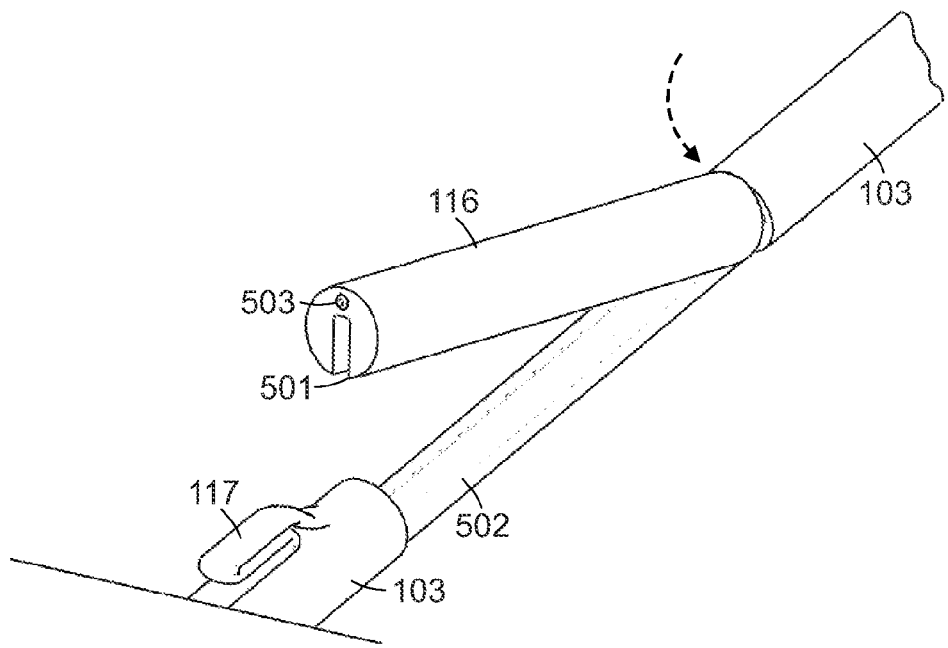
Figure 5E:
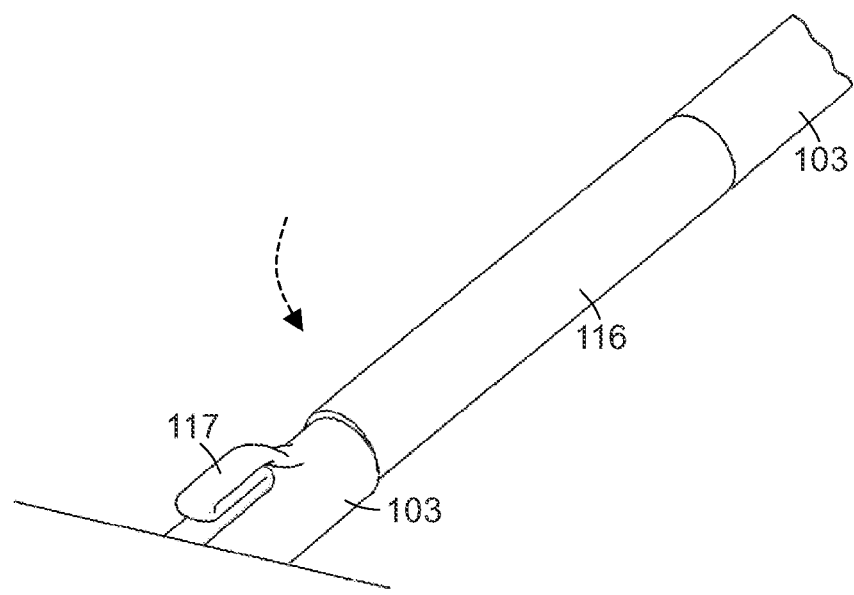
Figure 5F:
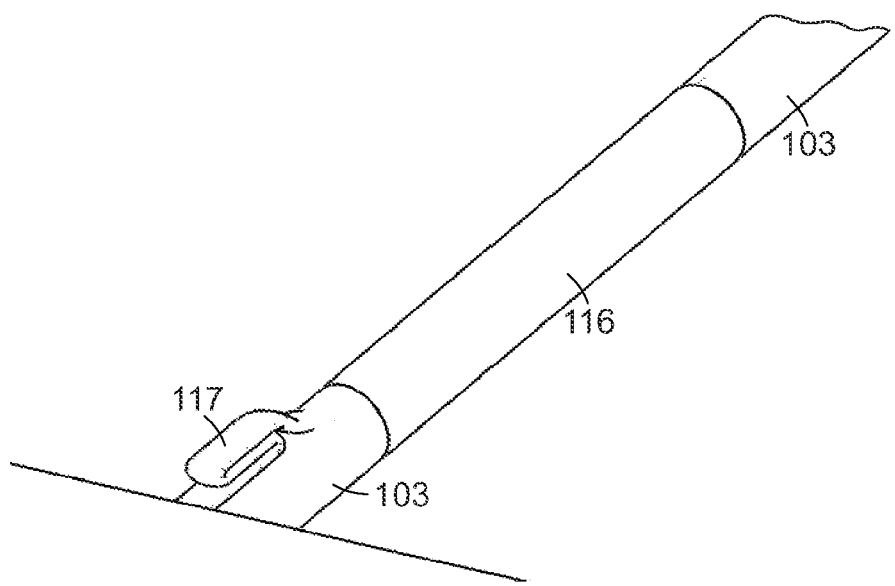
Figure 5G:
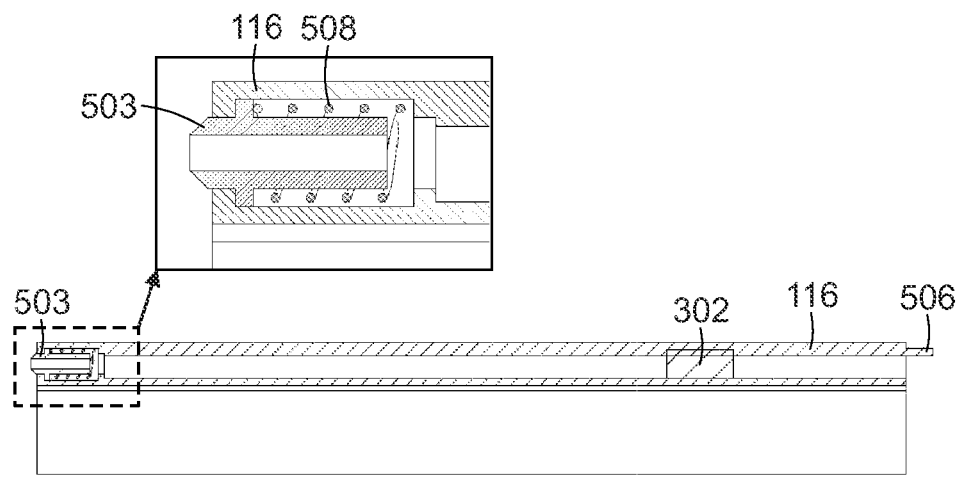
Figure 5H:
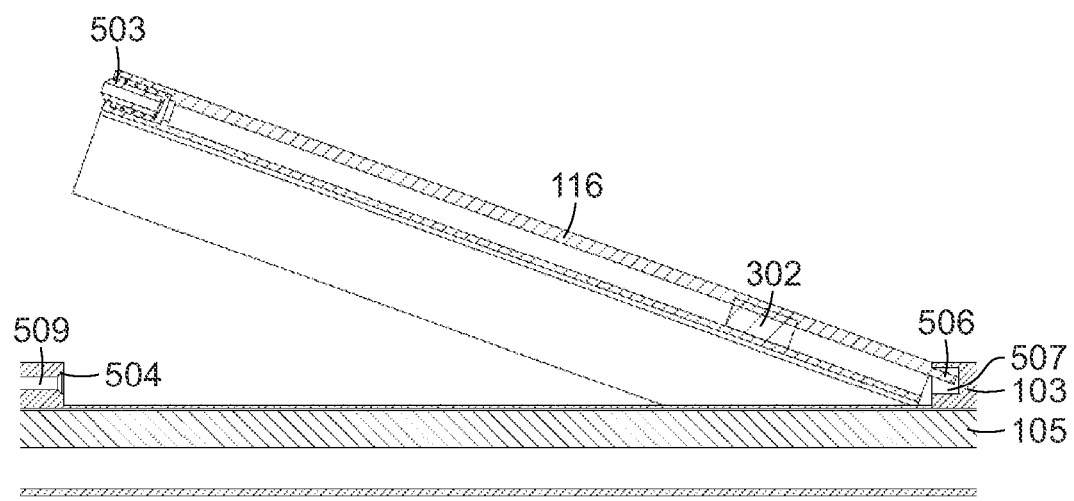
Figure 5I:
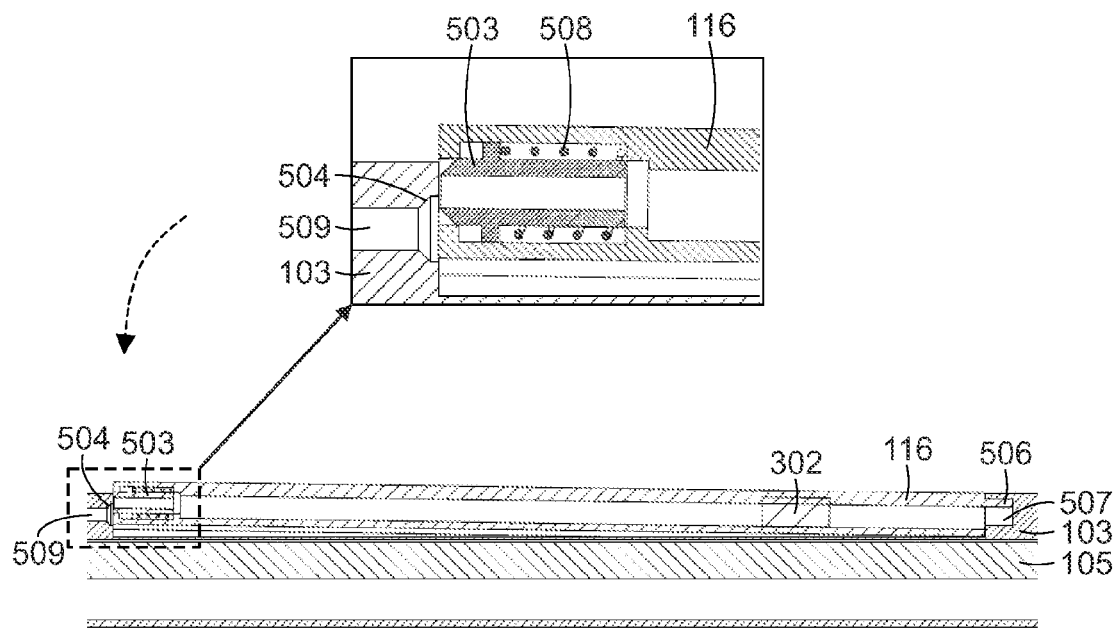
Figure 5J:
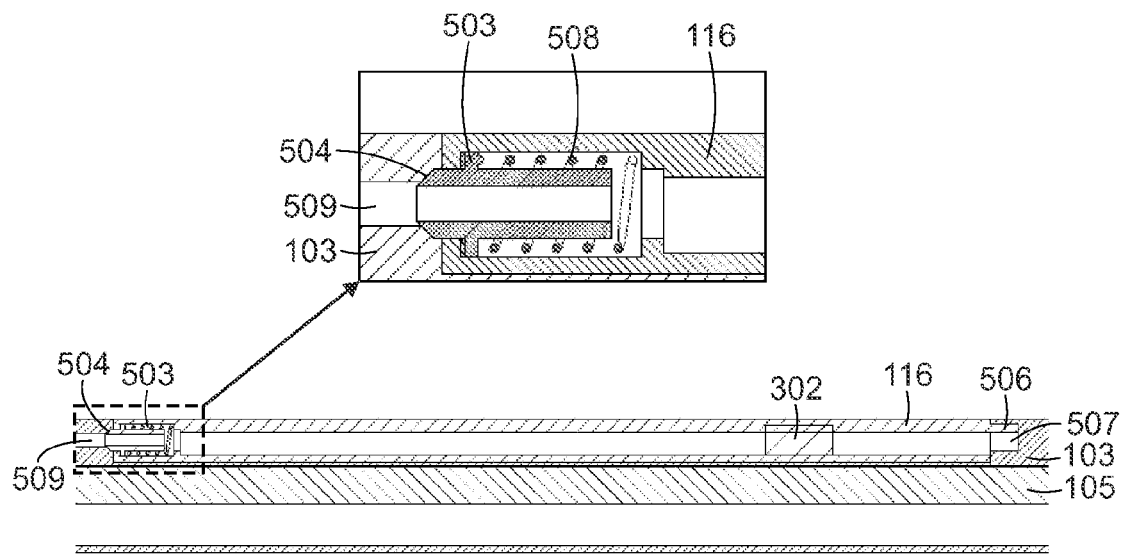

The glue passes from GR 116 into GDT 117 through a glue port 503 which is located at the distal end of GR 116 (see FIG. 5C). Said port 503 is adapted to be fitted into socket 504 at tube 103 (FIGS. 5G-5J).

Socket 504 is connected to GDT 117 via a hole 509 allowing glue 119 to flow from GR 116 to GDT 117 once GR 116 is completely coupled to tube 103.

Reference is now being made to FIGS. 5C-5J which illustrate the process of coupling the GR 116 to the DAD 100, namely to tube 103.

FIGS. 5C-5F illustrate the process in a 3D isometric view and FIGS. 5G-5J respectively illustrate the same process in a lateral cross sectional view.

FIGS. 5C-5J illustrate the initial stage of said reversible coupling.

A hook 506 is located at the proximal end of said GR 116. Said hook 506 is adapted to be inserted into socket 507 at tube 103 during said reversible coupling of said GR 116 to tube 103.

According to this embodiment, in order for the GR 116 to be coupled to the tube 103, said glue port 503 is spring-like coupled to said GR 116 such that during the coupling it can retract into the GR 116 (see FIGS. 5G-5J).

A spring 508 keeps said port 503 extruding out of GR 116 when said GR is not coupled to the tube 103.

At the first stage of insertion (FIGS. 5D—in 3D view and FIG. 5H in a 2D view) said hook 506 is inserted into socket 507. At the next stage (FIGS. 5E—in 3D view and 5I in a 2D view) the distal portion of said GR 116 is lowered toward tube 103 while hook 506 acts as a hinge between GR 116 and tube 103.

When port 503 is pressed against the edges of tube 103, it retreated inwardly as a result of the downward pushing forces. At the final stage (FIGS. 5F—in 3D view and 5J in a 2D view), port 503 is facing said socket 504, therefore port 503 is pushed forward by spring 508 into socket 504, allowing glue 119 to flow between GR 116 and GDT 117 while preventing any unwanted glue leakage.

Port 503, together with hook 506, are also holding GR 116 attached to tube 103.

Once the GR is secured to tube 103, the glue can flow from the GR 116 to the GDT 117 via a channel 509.

The following steps describe the entire procedure in a minimal invasive surgery whilst using the above described system:

1. The patch 106 is reversibly connected to the distal portion 101 of said DAD.
2. The GR 116 in assembled with the DAD (i.e., reversibly coupled to tube 103).
3. The DAD is transformed into its 'closed configuration' and patch 106 is folded/rolled in order to allow its insertion into the abdominal cavity.

4. The folded patch 106 together with the GDS 115 is inserted to a body cavity through a standard minimal invasive port, or through any other incision.
5. The patch 106 together with the attached glue dispensing tube 117 is unfolded by pulling the deployment leaver 113 (thus, transforming the distal portion 101 into its 'deployed configuration).
6. The glue is forced out form the GR 116, by pushing the piston 302.
7. The glue is dispensed through the nozzles, and spread on top of the patch 106 (the nozzles are either pre inserted into the patch or not—i.e. when a porous patch is used).
8. The patch 106 is brought to be in contact with the tissue.
9. The patch is held in place until the glue is stabilizes (i.e., at least partially cured), and a sufficient attachment is achieved.
10. The patch is disconnected from the deployment system.
11. The deployment system and thus the glue dispensing tube GDT 117 are pulled away.
12. The deployment system is closed (i.e., transforms from its deployed configuration to its 'closed configuration') and removed from the body cavity together with the GDT 117.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:
1. A system for closing an aperture in a biological tissue, the system comprising:
    a handle;
    an elongate shaft connected to the handle;
    a deployment scaffold connected to the shaft, the deployment scaffold including:
        first and second frame arms, wherein the deployment scaffold is configured to releasably retain a surgical implant; and
        proximal deployment arms and distal deployment arms hingedly connected to the first and second frame arms, wherein the deployment scaffold is configured to move from a retained position to a deployed position; and
    at least one adhesive dispensing system, the at least one adhesive dispensing system having at least one dispensing tube external to the deployment scaffold, the at least one dispensing tube extending along an outer surface of the first and second frame arms.
2. The system according to claim 1, wherein the adhesive dispensing system further comprises:
    at least one reservoir for holding adhesive;
    the at least one dispensing tube connected to the at least one reservoir; and
    at least one nozzle connected to the at least one dispensing tube.
3. The system according to claim 2, wherein the at least one reservoir is removable from the adhesive dispensing system.
4. The system according to claim 2, wherein the at least one reservoir comprises a breakable membrane.
5. The system according to claim 2, wherein the at least one nozzle is integrated with the deployment scaffold and the at least one nozzle is configured to dispense adhesive from a lower surface of the surgical implant releasably retained by the deployment scaffold.
6. The system according to claim 2, further including:
    at least two reservoirs, wherein each reservoir holds a different type of adhesive; and
    at least two dispensing tubes, each dispensing tube fluidly coupled to one of the reservoirs.
7. The system according to claim 2, further including:
    at least two reservoirs, wherein each reservoir holds a different component of a multi-component adhesive; and
    at least two dispensing tubes, each dispensing tube fluidly coupled to one of the reservoirs.
8. The system according to claim 2, wherein the nozzles are positioned such that they dispense adhesive in a common direction.
9. The system according to claim 1, wherein the dispensing system is configured to dispense adhesive onto the surgical implant while it is releasably retained by the deployment scaffold.
10. The system according to claim 1, wherein the system further comprises a biocompatible adhesive held within the adhesive dispensing system.
11. The system according to claim 10, wherein the adhesive is glue.
12. The system according to claim 11, wherein the glue is fibrin sealant or cyanoacrylate.
13. The system according to claim 1, wherein the deployment scaffold comprises a plurality of arms that are configured to move from a retained position to a plurality of deployed positions, wherein the arms hold the surgical implant.
14. The system according to claim 1, wherein the deployment scaffold is configured to allow for deployment of the surgical implant and retraction of the surgical implant while the surgical implant is within a patient's body.
15. The system according to claim 1, wherein the deployment scaffold is configured to allow for a plurality of deployment positions.

16. The system according to claim 1, wherein the deployment scaffold comprises an articulating member that allows for adjustment of the position and the orientation of the surgical implant relative to an aperture in tissue.

17. The system according to claim 1, further comprising a surgical implant.

18. The system according to claim 17, wherein the surgical implant is a patch.

19. The system according to claim 18, wherein the patch is porous.

20. The system according to claim 18, wherein the patch is comprised of surgical mesh.

21. The system according to claim 18, wherein the patch is non-porous.

22. The system according to claim 1, wherein the system is adapted for closing an aperture in an abdominal wall.

23. The system according to claim 1, wherein the elongate shaft is flexible.

24. The system according to claim 1, wherein the elongate shaft is rigid.

25. The system according to claim 1, wherein the first and second frame arms include connection clips connected to the first and second frame arms and configured to releasably hold the surgical implant.

26. The system according to claim 25, wherein the deployment scaffold further includes a central frame piece that is slidably connected to the elongate shaft and hingedly connected to the distal deployment arms, wherein the central frame piece slides from a distal position wherein the deployment scaffold is retracted to a proximal position wherein the deployment scaffold is deployed.

27. The system according to claim 1, wherein the system is configured such that the adhesive dispensing system dispenses adhesive onto the biological tissue prior to the surgical implant being attached to the biological tissue.

* * * * *